US006790652B1

(12) United States Patent
Terry et al.

(10) Patent No.: US 6,790,652 B1
(45) Date of Patent: Sep. 14, 2004

(54) METHOD AND APPARATUS FOR HIGH DENSITY FORMAT SCREENING FOR BIOACTIVE MOLECULES

(75) Inventors: Bernard Robert Terry, Frederiksberg C (DK); Kurt Marshall Scudder, Virum (DK); Per Olaf Gunnar Arkhammer, Helsingborg (SE); Ole Thastrup, Bikeroed (DK)

(73) Assignee: BioImage A/S, Soborg (DK)

(*) Notice: Subject to any disclaimer, the term of this patent is extended or adjusted under 35 U.S.C. 154(b) by 0 days.

(21) Appl. No.: 09/227,518

(22) Filed: Jan. 8, 1999

Related U.S. Application Data

(60) Provisional application No. 60/070,792, filed on Jan. 8, 1998.

(51) Int. Cl.$^7$ .............................. C12M 3/00; A01N 1/02
(52) U.S. Cl. ......................... 435/287.7; 435/4; 435/7.2; 435/7.92; 435/177; 435/178; 435/179; 435/180; 435/182; 435/395; 435/401; 435/286.1; 435/287.1; 435/287.7; 436/501; 436/34; 436/55; 436/147; 436/162; 436/164; 436/165; 436/169; 436/172; 436/174; 436/800; 436/809; 436/815; 422/50; 422/51; 422/52; 422/55; 422/56; 422/58; 422/68.1; 422/69; 422/81; 422/82.05; 422/82.07; 422/101

(58) Field of Search ..................... 435/4, 6, 7.1, 7.21, 435/7.72, 7.92, 7.8, 177–180, 70.1, 182, 242, 325, 395, 401, 286.1, 287.1, 287.7, 7.2; 436/501, 528, 529–531, 546, 164, 169, 170, 174, 177, 800, 809, 815, 34, 55, 147, 162, 165, 172; 422/51, 52, 50, 55, 56, 58, 60, 69, 81, 82.05, 82.07, 68.1, 101

(56) References Cited

U.S. PATENT DOCUMENTS

| | | | |
|---|---|---|---|
| 5,580,750 A | | 12/1996 | Doglia et al. .................. 435/32 |
| 5,756,351 A | * | 5/1998 | Isacoff et al. ................ 435/325 |
| 5,783,408 A | * | 7/1998 | Hamilton et al. .............. 435/29 |
| 5,856,083 A | * | 1/1999 | Chelsky et al. ................. 435/4 |
| 5,876,946 A | * | 3/1999 | Burbaum et al. ............. 435/7.1 |
| 5,976,813 A | * | 11/1999 | Beutel et al. ................. 435/7.1 |
| 6,200,762 B1 | * | 3/2001 | Zlokarnik et al. ............ 435/7.1 |
| 6,214,563 B1 | * | 4/2001 | Negulescu et al. ........... 435/7.1 |

FOREIGN PATENT DOCUMENTS

| | | |
|---|---|---|
| EP | 0 653 637 A2 | 5/1995 |
| WO | WO 91/19187 | 12/1991 |
| WO | WO 94/02515 | 2/1994 |
| WO | WO 97/16569 | 5/1997 |
| WO | 99/30154 | 6/1999 |
| WO | WO 9930154 | 6/1999 |

OTHER PUBLICATIONS

Sittampalam, et al., "High–throughput screening:advances in assay technologies", Curr. Op. Chem. Biol., 1:384–39, 1997.

Rogers, et al., "Light on high–throughput screening:fluorescense–based assay technologies", Drug Discovery Today, vol. 2: 156–160, 1997.

Burbaum, et al., "New technologies for high–throughput screening", Curr. Op. Chem. Biol., 1:72–78, 1997.

(List continued on next page.)

*Primary Examiner*—Christopher Chin
*Assistant Examiner*—Gailene R. Gabel
(74) *Attorney, Agent, or Firm*—Birch, Stewart, Kolasch & Birch, LLP

(57) ABSTRACT

A method and apparatus for screening an array of test compounds for bioactivity by contacting an array of test compounds with a detector layer capable of detecting bioactivity, and detecting a detector layer response. The detector layer is comprised of physiologically viable cells. The method and apparatus allow a large number of test compounds to be simultaneously assayed in parallel without the need for complex fluidic devices.

17 Claims, 12 Drawing Sheets

3-D sectional representations of portions of the test-array/detector layers: not to scale

OTHER PUBLICATIONS

Silverman, et al., "New assay technologies for high-throughput screening", Curr. Op. Chem. Biol., 2:397–403, 1998.

Rose, et al., "The successful partnership of biotechnology based screen development with high throughput screening", Network Science 1–12, 1998.

Schullek, J.R. et al., "A high-density screening format for encoded combinatorial libraries: Assay miniaturization and its application to enzymatic reactions", Anal. Biochem., 246: pp. 20–29, 1997.

Schena, M. et al., "Quantitative monitoring of gene expression patterns with a complementary DNA microarray", Science, vol. 270: 467–470, Oct. 20, 1995.

* cited by examiner

Fig. 1 Schematic view of equipment; not to scale

Fig. 2
Side views of test stage; not to scale
a) 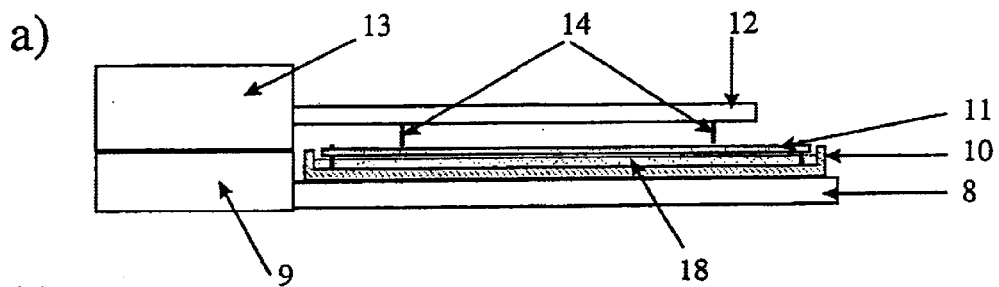
b) 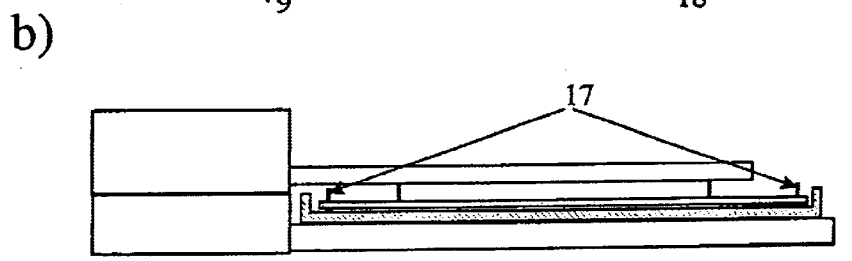
c) 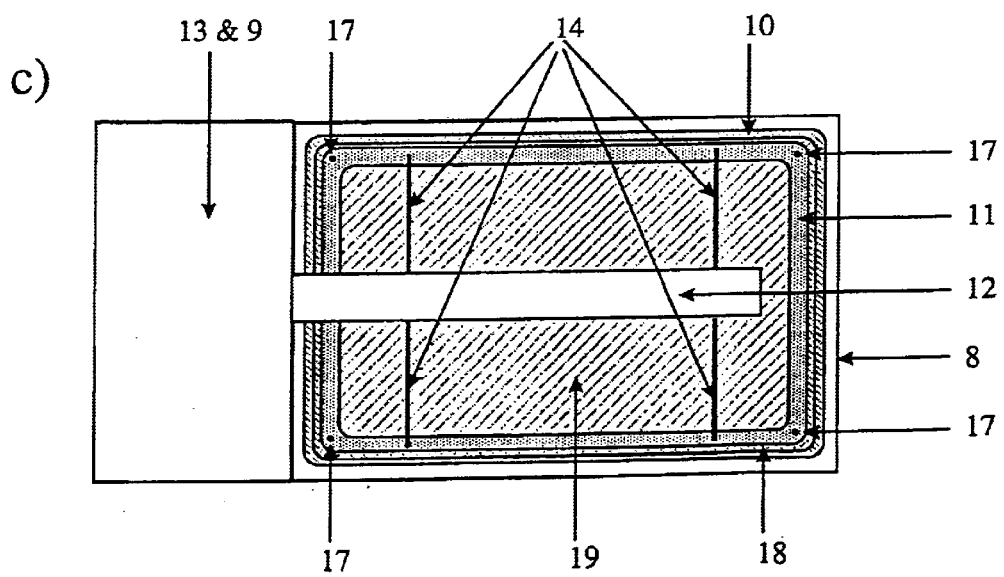
Top view of test stage; not to scale

3-D sectional representations of portions of
the test-array/detector layers: not to scale Fig. 5
a)
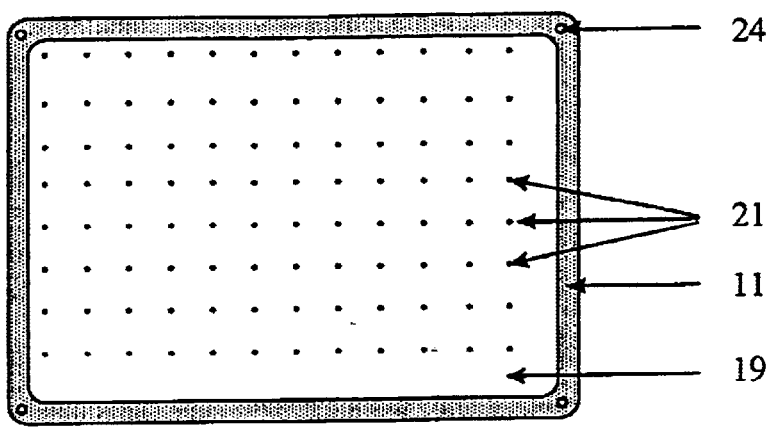
b)
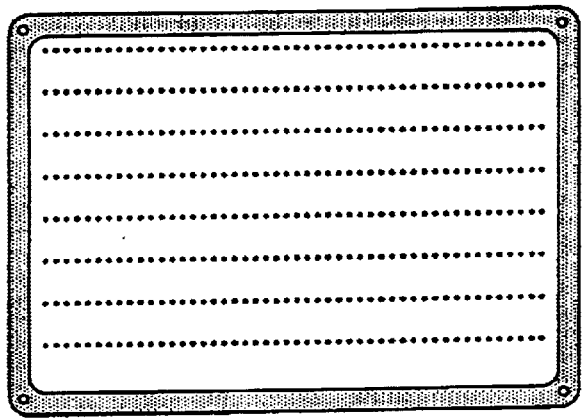
c)
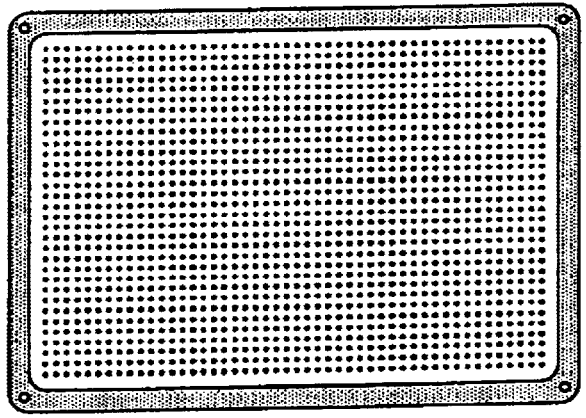

FCCP Dose-response
(50, 5, 0.5, 0.05 and 0.005 µM, 5 x 5 grid)

Ionomycin and Thapsigargin responses

METHOD AND APPARATUS FOR HIGH DENSITY FORMAT SCREENING FOR BIOACTIVE MOLECULES

This nonprovisional application claims priority under 35 USC §119(e) on U.S. Provisional Application No. 60/070,792 filed on Jan. 8, 1998, which is herein incorporated by reference.

FIELD OF THE INVENTION

The invention relates to a method and apparatus for screening large numbers of molecules for biological activities.

BACKGROUND OF THE INVENTION

Current technology is able to generate large numbers of molecules with potential therapeutic value. These compounds include products of combinatorial or traditional chemistry, natural products, proteins isolated by one- or two-dimensional gel electrophoresis, or compounds secreted from or expressed by natural or genetically modified animal, plant, microbial or fungal cells, or displayed by natural or genetically modified viral or phage particles.

The practice of screening large libraries for a compound having a specific biological activity is routinely used in new drug discovery. Screening methodologies include binding assays or functional assays. A binding assay identifies compounds of interest by affinity to cells or cell products, and may include detection methods such as the use of fluorescent, luminescent, or radioactive labels. Functional assays may also be used, for example, determination of effects on gene expression.

Screening methods have been developed which achieve very high throughputs of test compounds. Such methods are termed Ultra High Throughput Screening (UHTS). The present generation of UHTS machines rely upon essentially serial additions of test compounds, usually one test compound per discrete test well. Test well array densities range from between 96 to 3456 wells per plate. Such UHTS machines require sophisticated technologies to dispense microvolumes of many different fluids to selected locations, and also require that the detecting surface for each test molecule generally be separated from other detecting surfaces within the array.

Visualization of intracellular function using luminescent (fluorescent or bioluminescent) probes has become one of the mainstay techniques in modem cell biology. Using traditional optical microscopes with quantitative detectors in place of the human eye, both the concentration and distribution in the cell of a variety of intracellular molecules of interest can be measured. While luminescent probes can be measured in large populations of cells using other techniques, imaging is critical for studying single cells or small populations of cells. Most of these probes can be introduced non-invasively into cells and will, depending on the detection system, allow characterization of cellular events in high temporal resolution (microseconds to seconds) and high spatial resolution (nanometers to micrometers). This probe technology, in combination with the technology of cellular imaging, has enabled monitoring of complex, cross-reacting intracellular events not previously accessible by conventional techniques. The use of luminescent probes for cell-based screening is described in PCT publication WO 97/45730.

There is a need to develop a method which allows simultaneous screening of large numbers of test compounds for biological activity and potential therapeutic use while avoiding the complications associated with dispensing multiple microvolumes of many different fluids.

BRIEF SUMMARY OF THE INVENTION

The invention is directed to a screening method which eliminates the need for delivering microfluid volumes and allows simultaneous parallel screening of large numbers of test compounds. Accordingly, the invention is drawn to a method for screening test compounds for bioactivity, by contacting an array of test compounds with a detector layer capable of detecting bioactivity, wherein a cell response is indicative of bioactivity.

In the method of the invention, a detector layer may be comprised of physiologically viable cells, which in a specific embodiment form a monolayer. The detection step may comprise a change in a fluorescence or luminescence property of the cell. In a specific embodiment, detection is determined with an illumination system capable of exciting the fluorescence of the detector layer with any of a number of previously selected wavelengths with defined order and of defined time duration.

In related embodiments, the detector layer may be scintillant plastic, a pH sensing surface, or a temperature sensitive surface. One example of a scintillant plastic is Cytostar plates (Amersham). Cells are grown on top of the scintillant plastic, radio-labelled ligand is applied to the cells, and then displaced by test compounds which are competitive to those ligand receptors. The signal is a reduction in scintillation at the point in the detector layer corresponding to an "active" ligand in the array of test compounds. A pH sensing surface may also be used (Molecular Devices Corp.) incorporated into the solid support upon which cells in the detector layer are growing. Many changes in cellular activity result in changes in proton extrusion from cells, and hence localised changes in the pH of medium around responding cells. Temperature sensing surface, such as a sensitive calorimetric or fluorescent liquid crystal layer, may also be incorporated into the substrate upon which the cells are growing. Such a detector layer is useful for metabolic responses which give rise to changes in heat flux from cells.

In specific embodiments, the detector layer is supported by an optically clear substrate. Further, the detector layer may be held stationary in the field of view of the lensing sytem and camera and the sample surface is moved into contact with the detector layer during the course of measurement. In another embodiment, the sample surface is held stationary in the field of view of the lensing system and camera and the detector layer is moved into contact with the sample surface during the course of measurement.

The test compounds screened in the method of the invention may be generated by a variety of methods known to the art, including those generated on a solid support by combinatorial chemistry, or by one- or two-dimensional gel electrophoresis.

The method of the invention is a high throughput system for parallel screening of a large number of test compounds. In one embodiment of the method of the invention, 96 to 10,000 test compounds are simultaneously screened for bioactivity in an assay; in a more specific embodiment, 96 to 6,144 test compounds are simultaneously screened for bioactivity.

In a related embodiment, the invention is drawn to a method for screening test compounds for bioactivity, by (1) contacting a solid support comprising an array of test compounds with a liquid layer, wherein the liquid layer is in immediate contact with a detector layer and wherein each test compound comes into contact with a localized portion of the liquid layer; and (2) registering a response of the detector layer to the test compound, wherein a bioactive test compound is identified.

In a related embodiment, the invention is drawn to a method for high throughput screening of test compounds for bioactivity, comprising (a) contacting a solid support comprising an array of multiple test compounds with a detector layer, wherein each test compound comes into contact with a localized liquid which is in contact with the detector layer; and (b) detecting a response of the detector layer to the test compound, wherein a response is indicative of a bioactive compound.

In another related embodiment, the invention is drawn to a method for simultaneously exposing an array of test compounds with a detector layer, comprising the steps of (a) contacting an array of test compounds on a solid substrate with a porous membrane which is in contact with a liquid layer surrounding a detector layer, (b) allowing the test compounds to move via the porous membrane to the liquid layer surrounding the detector layer, and (c) detecting a response in the detector layer where the detector layer comprises a layer of physiologically viable cells.

In another related embodiment, the invention is drawn to a method for simultaneously exposing an array of test compounds with a detector layer, comprising the steps of (a) contacting an array of test compounds held on a porous membrane or non-porous substrate with a liquid layer overlaying a detector layer, (b) allowing the test compounds to move from the porous membrane or non-porous substrate into the liquid layer overlaying the detector layer, and (c) detecting a response in the detector layer where the detector layer comprises a layer of physiologically viable cells.

The invention further features an apparatus for screening an array of test compounds for bioactivity, comprising (a) a solid support comprising an array of test compounds, (b) a porous membrane, and (c) a detector layer, wherein a liquid layer is between the porous membrane and detector layer, and wherein the test compounds contact the detector layer by movement via the porous membrane.

One advantage of the method of the invention is that it allows massively parallel screening of a large array of test compounds for biological activity. When physiologically viable cells are the detector layer of the invention, they are maintained under physiologically viable conditions. Provision of these conditions requires the use of solutions able to supply essential nutrients and buffer pH changes normal to the continued growth of physiologically viable cells. Such solutions may be complete cell culture media (i.e. any of those commercially available, for instance from Life Technologies Ltd.), optionally supplemented with antibiotics and serum preparations for optimal cell growth conditions. Buffer solutions may also be of the type known as "chemically defined". Cells will also require controlled temperature conditions, in the range 20° to 37° C., and the provision of gases essential to continued cell growth and maintenance of buffer capacity ($O_2$, and optionally 5% $CO_2$, depending on the type of buffer being used).

These and other objectives, advantages, and features of the invention will become apparent to those persons skilled in the art upon reading the details of the method as more fully described below.

BRIEF DESCRIPTION OF THE DRAWINGS

The foregoing features of the present invention may be fully understood from the following detailed disclosure of a specific preferred embodiment in conjunction with the accompanying drawings in which:

FIGS. 2a–c: FIGS. 2a and 2b are side view of the test stage (not to scale); FIG. 2c is a top view of the test stage. A supporting stage 8 has a rectangular central aperture the shape and size of which is the same as the area 19 of FIG. 2c. The position of stage 8 is adjusted in the horizontal and vertical axes by the 3-axis positioner 9. Components of the test stage shown include, solution layer 18, (not shown: detector layer 20 and array of test compounds 21 in FIGS. 3 and 4). The array 21 is held away from the liquid layer by pins 17 which pass through holes (24 in FIG. 5) in the corners of the frame 11. Arm 12 is moved down by the drive unit 13, and the four sprung contacts 14 it bears exert pressure on the frame 11 moving it down the guide pins 17 and into close proximity to the upper surface of 10, from which it is separated by a thin liquid layer 18.

FIGS. 5a–c are schematics illustrating transfer printing of an array of compounds onto a surface of a track-etched membrane. Compounds are stored in 16 separate 96-well microtitre plates and defined amounts are transferred from each individual plate simultaneously by a 96-pin printing head to the surface 19 (FIG. 5*a*). The contents of each successive 96-well plate are printed at a slightly offset position, generating an array of 384 compounds after 4 such printing operations (FIG. 5*b*), and a full array of 1536 compounds after 16 printing operations (FIG. 5*c*). The number of discrete spots in an array can be incremented by additional printing steps to any required total that is consistent with the space available on surface 19.

DETAILED DESCRIPTION

Figure 1:
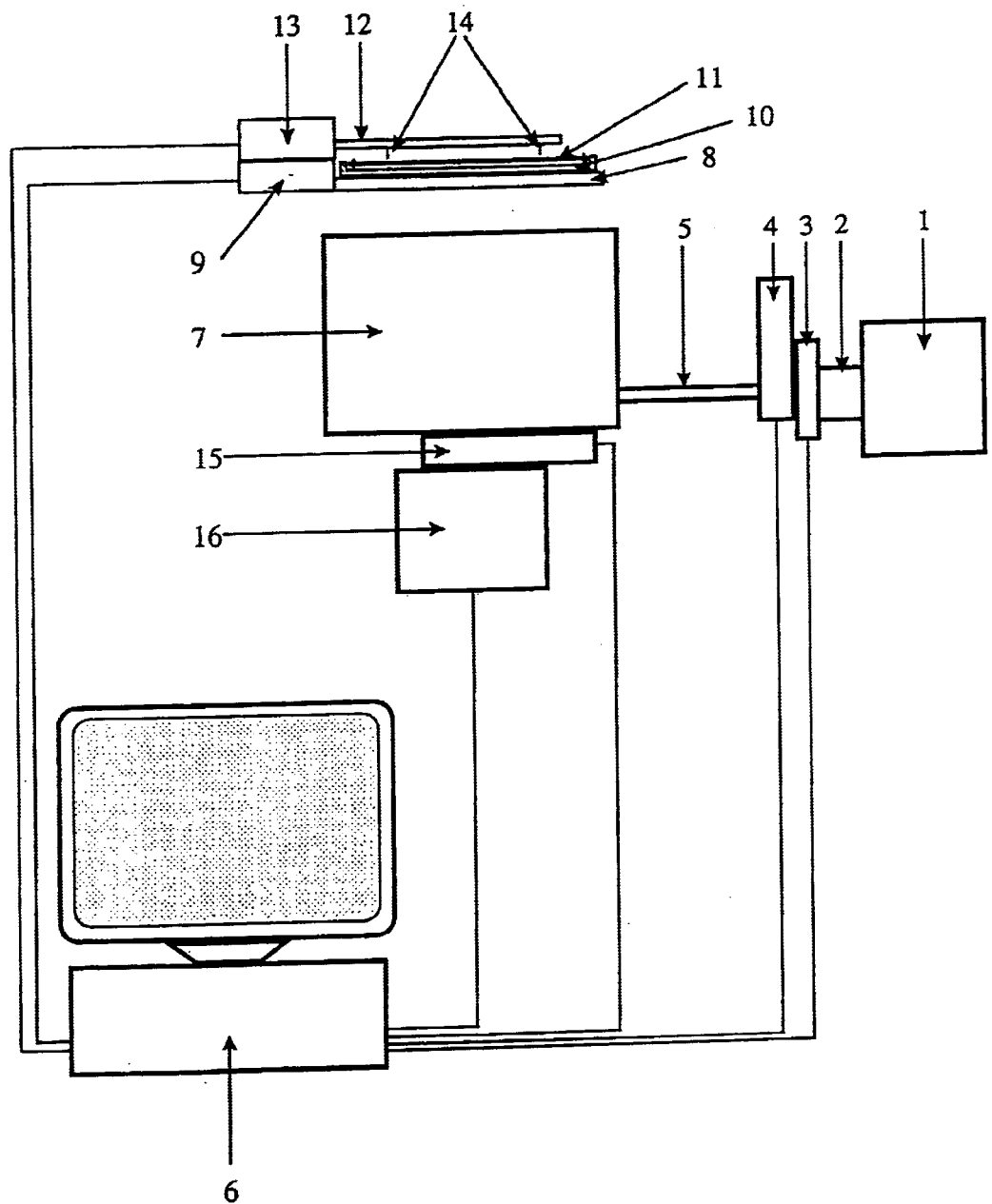
FIG. 1 is a schematic representation of the apparatus useful in one specific embodiment of the invention: Light from a high energy light source 1 is collected and collimated by unit 2, directed through a shutter assembly 3 and passes through a excitation filter-changer 4. A light guide 5 directs excitation light into the lensing and epi-illumination optics housed in unit 7. Excitation light emerging from 7 illuminates the horizontal detector layer located in the multi-component assembly having two solid layers 10 and 11 fixed relative to a supporting stage unit 8. Layer 11 is moved vertically downward on guide pins (17 FIG. 2b) controlled by arm 12 driven by unit 13. Four sprung contacts 14 attached to 12 press upon the frame of layer 11 to drive it downwards as arm 12 descends. Specified devices (3,4, 9, 13, 15,16) are controlled by central processing unit 6 which issues commands and collects data and status information from the devices attached to it. Unit 6 includes a central processing unit, RAM, multi-channel serial input/output cards with onboard A/D and D/A converters, one of which cards controls the camera 16 and captures images from it.

Before the present method and solutions used in the method are described, it is to be understood that this invention is not limited to particular methods, components, or solutions described, as such methods, components, and solutions may, of course, vary. It is also to be understood that the terminology used herein is for the purpose of describing particular embodiments only, and is not intended to be limiting, since the scope of the present invention will be limited only by the appended claims.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference to disclose and describe the methods and/or materials in connection with which the publications are cited.

By "high throughput screening" is meant a method able to screen large number of test compounds for biological activity within a given machine time (i.e. at a rate anywhere from 100 to 100,000 compounds per hour per machine).

The term "parallel screening" refers to a method by which very many compounds are applied simultaneously to the detector layer, and similarly, signals from that detector layer are collected contemporaneously rather than sequentially.

By "array" is meant a regular two-dimensional arrangement of test compounds by which compounds are disposed at the nodes of a rectilinear grid pattern whereby a compound position can be identified by a simple 2-dimensional coordinate.

A "detector layer" means any two-dimensional system which can be used to report biologically relevant information. In one specific embodiment of the method of the invention the detector layer is a monolayer of physiologically viable cells loaded with a fluorescent reporter dye such as Fluo-3 or JC-1 (Molecular Probes, Eugene, Oreg., USA). In another embodiment, the detector layer is a "reactive sensing surface" such as a scintillant plastic (Cytostar assay plates; Amersham Pharmacia Biotech UK Ltd., Little Chalfont, Bucks, UK).

By "bioactive" or "bioactivity" is meant an action or influence of a test compound upon the detector layer which results in a response from the detector layer that has direct biological significance or can be interpreted as being a biologically relevant response. Bioactive agents have the ability to effect physiological parameters of physiologically viable cells and tissues. Bioactivity includes inducing or suppressing the expression of a protein, activating or inhibiting transcription of a gene, and/or affecting cellular function(s) such as, for example, intracellular movement and storage of calcium ions, intracellular movement or distribution of proteins or protein assemblies, membrane transportation as in vesicle traficking for example, and active or passive ion movements such as are important in the generation of electrical potential differences across biological membranes.

The capacity of a test compound to affect a detector layer, i.e. bioactivity, may be determined in a number of ways known to the art. In specific embodiments of the method of the invention, bioactivity is determined by changes in fluorescent properties or movements of fluorescent probes present in the detector layer which indicate changes in ionic content, cell metabolism, growth or viability. In a preferred method of the invention, physiologically viable cells form the detector layer and have specific protein components tagged with a fluorescent agent, such as green fluorescent protein (GFP); changes in GFP fluorescence or distribution within cells indicate a particular cellular response which may be selected for identification of bioactivity. The phrase "a change in fluorescence" means any change in absorption properties, such as wavelength and intensity, or any change in spectral properties of the emitted light, such as a change of wavelength, fluorescence lifetime, intensity or polarization.

A "solid support comprising an array of multiple test compounds" or similar terms, mean a fixed matrix to which test compounds have been applied. As an example, the solid support of the invention includes a membrane or other surface comprising an array of printed test compounds. In one specific embodiment of the invention, the test compounds are deposited as discrete spots on a porous track-etched polyester membrane 10 to 20 microns thickness, the spots being between 10 microns to 2 mm diameter. The quantity of compound contained in each discrete spot will depend on the concentration of the stock solution from which it was derived, and the volume of that stock solution applied to the support. In another specific embodiment of the invention, compounds are printed onto a non-porous solid support which is optically clear.

By "test compounds" is meant a number of chemical compounds which are to be screened for ability to effect physiological parameters of a cell or tissue. In one embodiment, the test compounds are proteins or peptides generated by combinatorial protein chemical methods known to the art. In another embodiment, the test compounds are chemical compounds generated by conventional or combinatorial chemistry methods known in the art. In another embodiment, the test compounds are chemical compounds which are naturally occurring compounds more or less purified from their native state, are the products of genetically engineered cells, or are viral or bacteriophage particles engineered to display compounds upon their surfaces (phage display). In another embodiment, test compounds are separated by one- or two-dimensional gel-separation techniques as known in the art. The gels and the compounds they contain are applied so as to contact the detector layer directly.

In one embodiment, the detector layer is an undemarcated area of physiologically viable cells growing on a flat culture surface. The cells on this surface may or may not be grown to confluence, may be transformed and/or engineered cells, or directly derived from animal tissues and grown as primary cell culture.

In one embodiment, a test compound reaches the detector layer by movement from a porous membrane to a liquid layer immediately overlaying the detector layer. A variety of commercially available porous membranes are useful in the method of the invention. A preferred porous membrane is a track-etched polyester or polycarbonate support in which parallel channels of closely similar size are formed by a selective etching process following exposure of the membrane to a source of high energy ions. The method of the invention allows each test compound affixed to a solid support to come into contact with a limited fluid volume, which fluid volume is in immediate contact with the detector layer. In one embodiment, each test compound contacts the detector layer by movement through a liquid-containing channel directly adjacent to the detector layer.

Generally, the invention is drawn to a method for high throughput screening of test compounds; by contacting a solid support comprising an array of multiple test compounds with a detector layer, wherein each test compound comes into contact with a localized liquid which is in contact with a detector layer, and detecting a response of the detector layer to the test compound, wherein a bioactive test compound is identified.

The high density format screening system (HDFS) of the invention rests in part on the realization that the delivery of test compounds to detector surfaces can be greatly simplified by doing away with the need for complicated microfluidics. Test compounds are applied to the detector surface in a massively parallel manner, and the method is applicable to a large range of different types of test compounds and solutions thereof in all commonly useful solvents.

Central to the specific embodiments of the method and apparatus of the invention, described below, is the use of physiologically viable cells as detectors, their responses being signaled via changes in the fluorescent or luminescent properties of various specific probes located within. However many different types of detector systems could be used in place of probe loadedcells in such a system, for example, appropriate variants of Scintillation Proximity Assay (SPA) systems such as scintillant plastics (Cytostar, Amersham Pharmacia Biotech) and enzyme-linked immuno-sorbent assay (ELISA) systems (Amersham Pharmacia Biotech).

The array of test compounds is formatted to have the same dimensions as the detector surface. In one specific embodiment of the invention, array and detector layers have a width of 8 cm and length of 12.5 cm, so as to fit within the format of conventional 96-well or 384-well microtitre plates. Preparation of the test arrays will depend on their origin.

Current methods for the production of single compounds by combinatorial methods are under development which involve miniaturization and patterned arrays of tethered solid-phase substrates. Thus, test compounds generated by combinatorial methods can be used to synthesize an array directly or indirectly on a carrier sheet. In one embodiment, vapor phase solubilization is used to produce a test compound array on the synthetic substrate, followed by a printing process of the test compound array on to an absorbent membrane. In this embodiment, the test array is the printed membrane. An advantageous feature of this method is that multiple copies of the same test array can be produced at one time to be screened against multiple cell systems for specific activities which minimizes stock handling from library archives. In another embodiment, compounds are delivered directly to the detector layer from the arrays of miniaturised reaction vessels that comprise high density microfluidics chips as are being developed by such companies as Orchid Biocomputer, Inc. (Princeton, N.J., USA).

Currently most compounds to be screened come in 96-well format. However, the 96-well format can be altered by repeated off-set printings, to any chosen density of format that the transfer substrate and assay can support. The optimum density of compounds in the test array will depend very much on the fraction of compounds in an array which generate bioactive responses in the detector layer ("hit rate"). The hit rate will depend on how well the compound library being tested matches the targets in the assay. If the hit rate is low, e.g., in the range of 1:20,000–100,000 compounds tested, a test array with center to center spacing of 200 $\mu$m (giving 240,000 separate compounds in a 12 cm×8 cm area) may be preferable, providing 2 to 10 hits per plate. At a spacing of 1 mm, 9,600 test compounds may be screened simultaneously. The density of the format may be adjusted as required without requiring any changes in the hardware used to perform the re-formatting; rather, adjustment may be made in the degree of off-set and the number of print operations used per array.

Fluorescence imaging provides a way to monitor physiological responses of physiologically viable cells in a non-invasive manner. Ion- and voltage-sensitive probes, as well as the new generation of recombinant fluorescent probes, for instance, hybrid proteins comprising fusions of green fluorescent protein variants (GFPs) to cellular proteins involved in intracellular signaling, can be used singly or in combination to report on many aspects of cellular microphysiology. Due to the strong fluorescence of GFP, the luminescence of cells expressing the probes may easily be detected and analyzed by employing a combination of fluorescence microscopy and image analysis. Furthermore, these probes described are easily introduced into cells, as they can be expressed in the cells of interest after transfection with a suitable expression vector.

Recombinant probes for second messengers and enzyme activity, such as kinase activity, are not only useful in basic research but also in screening programs aimed at find compounds that affect intracellular concentrations of cAMP and protein kinase activity are based on receptor binding and/or immuno detection and/or reporter gene expression. The recombinant probes-used here allow development of a new type of screening assay to monitor immediate and transient changes of cAMP concentration and protein kinase activity in intact physiologically viable cells.

The HDFS method of the invention monitors the response of cell populations to test compounds. Lens systems are currently available which can simultaneously epi-illuminate and image the fluorescence from areas in excess of 8.5×13 cm, the size of a standard 96-well plate. The detection method used herein collects a variety of fluorescent signals from all cells in a field, with responses from discrete areas of the field being apparent in the real image of the fluorescence from that field as formed on the surface of the photosensitive detector (imaging camera).

Figure 3:
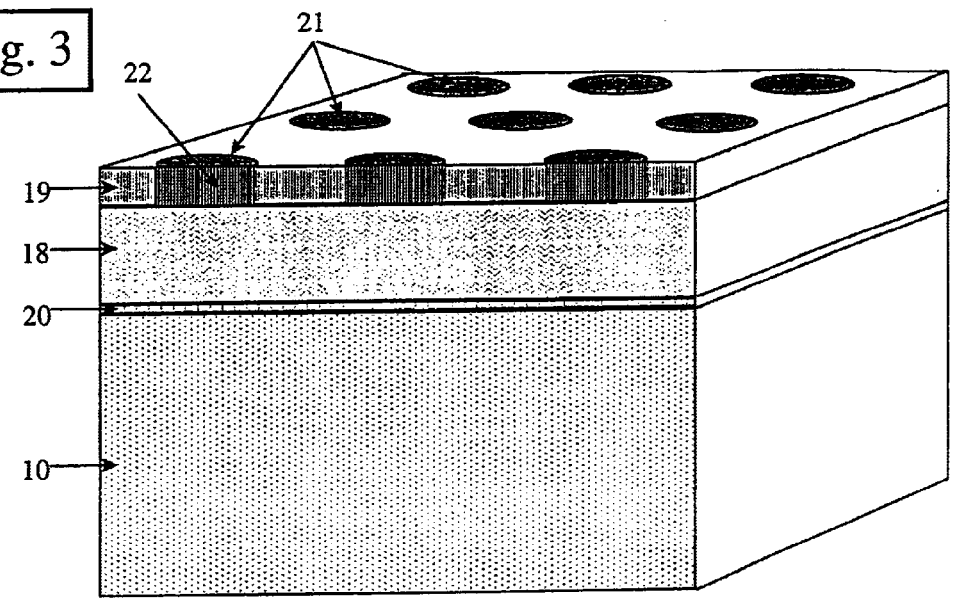
FIG. 3 is a schematic showing the relative positions of the different layers in the test-array/detector layers used in one specific embodiment. The layers are depicted in apposition, as they would appear after arm 12 has pushed component 11 down the support pins 17. An array of discrete spots of test compounds 21 on a porous membrane 19 is in contact with a liquid layer 18 overlaying the detector layer 20 which is supported by an optically transparent solid substrate 10. The compounds fill the parallel capillary spaces in the track-etched membrane 22.

In a first embodiment of the method of the invention, delivery of large arrays of test compounds to cells is achieved with test compounds which are present on or transferred to a porous carrier sheet. In specific embodiments, test compounds are printed on the carrier sheet, and the sheet is applied (overlaid) to a field of cells of the same area. The test compounds reach the detector cells by movement through a localized buffer layer immediately in contact with an area of the detector cell layer. This embodiment is shown in the schematic of FIGS. 2 and 3.

Porous carrier sheets can be used for delivery of test compounds. Test compound arrays are applied to porous carrier sheets by a variety of methods known to the art. For example, an array of test compounds may be transferred and fixed to the carrier sheet by the method of contact printing, whereby an array of inert flat-ended pins (e.g. made of stainless steel) is used to transfer defined volumes of individual test compounds (in the range 2 nl to 2 $\mu$l) in solution form to discrete points on a dry carrier sheet.

A porous membrane useful in the delivery of test compounds is a membrane constructed of a non-absorbent material with pores of regular and defined diameter which traverse the membrane directly from the upper to the lower side. The property of orthogonal capillarity is useful in these membranes to limit lateral spread of test compounds applied to the membranes as discrete spots of liquid, since it is important that the compounds remain as discrete spots upon the membrane. A variety of membranes of different thicknesses, materials, and pore densities are commercially available from a number of manufacturers. For example, porous membranes useful in the method of the invention include a track-etched polycarbonate or polyester membrane (Corning Costar or Whatman/Polyfiltronics). These are available in thicknesses from 6 to 23 microns, with pores of 14 to 0.015 microns, at 100,000 to 1,000,000,000 pores/cm$^2$. For delivery of test compounds with maximum ease of handling and loading of test compounds, polycarbonate or polyester membranes are preferred, particularly of a thickness of greater than 10 microns, with pores between 1 and 10 microns diameter at densities of between 20,000,000 to 100,000 pores/cm$^2$, respectively. Membranes which are useful in the method of the invention include Nucleopore® (Corning Costar), Poretics® Black (Osmonics), and Anopore (Whatman International Ltd., Maidstone, Kent).

Alternative membranes useful for the delivery of compounds include cast cellulose acetate or nitrocellulose membranes such as Immobilon (Millipore Corp., Bedford, Mass., USA), or (Membra-fil®), or PTFE membranes (Filinert®), or glass fiber filters (Corning Costar). These thicker membranes encourage lateral spread of liquid samples applied to their surfaces, but by virtue of being thicker could thus be used to deliver larger amounts of compounds. PTFE-based membranes are particularly useful for compounds supplied dissolved in aggressive solvents. Track-etched and cast cellulosic membranes may also be given hydrophilic or hydrophobic surface treatments. It is useful to have membranes whose surfaces have defined wettability properties.

When the test compound is soluble, the compound will dissolve into the buffer upon contact with the buffer medium, and directly contact the detector layer immediately underlying the buffer layer. In this embodiment, the test compounds dissolve upon contact with the buffer medium, and fall vertically onto the detector layer as a result of having a higher density than the surrounding liquor. It is generally preferred that the thin buffer layer between the test compound membrane and detector layer not be stirred significantly by convection. At the detector layer, the vertical fall of a solution of test compound is expected to spread radially by displacement and diffusion. The radial extent of a measured response may thus be use as an indicator of the potency of the compounds involved. Test compounds of limited solubility, such as those expressed on the surface of a carrier system, for instance, a cell membrane, viral or phage particle, must be brought into very close proximity, including direct contact, with the detector layers.

The detector layer may be a continuous or non-continuous layer of physiologically viable cells. In a specific embodiment, the detector layer is a continous cell monolayer corresponding in size to the test compound array. In more specific embodiments, thin glass substrate, suitably tissue culture treated is preferred for fluorescent probes requiring excitation wavelengths below 400 nm.

Physiologically viable cells are defined by such parameters as oxygen consumption, membrane potential, mitochondrial potential and cytoplasmic ion balance. Provision of these conditions requires the use of solutions able to supply essential nutrients and buffer pH changes normal to the continued growth of physiologically viable cells. Such solutions, well known to the art of cell culture, may be complete cell culture media optionally supplemented with antibiotics and serum preparations for optimal cell growth conditions. Cells will also require controlled temperature conditions, in the range 20° to 37° C., and the provision of gases essential to continued cell growth and maintenance of buffer capacity ($O_2$, and optionally 5% $CO_2$, depending on the type of buffer being used).

Figure 4:
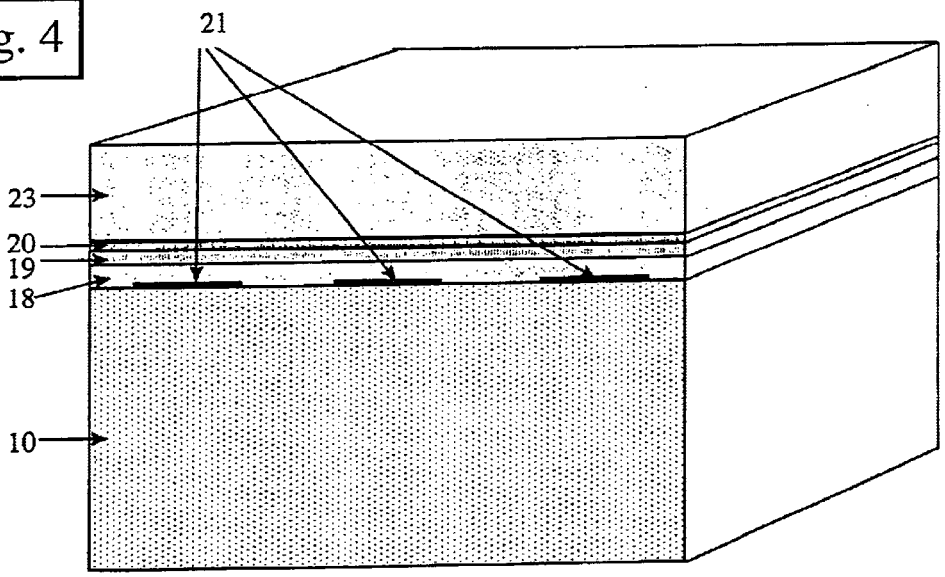
FIG. 4 is a schematic drawing of a second embodiment of the screening method of the invention. The layers are depicted in apposition, as they would appear after arm 12 has pushed component 11 down the support pins 17. A detector layer 20 supported on an optically clear porous membrane 19, and overlaid by a liquid layer 23, is placed onto an optically clear solid substrate 10 bearing an array of test compounds 21. The thin space 18 between components 19 and 10 is filled with solution. This solution is largely transferred as a thin film on the underside of the clear porous membrane, originating from the medium in culture unit (not shown) in which the detector layer has been generated. Some of this solution may also come from 23 having passed through the porous membrane 19. Bioactivity is detected by measuring changes in fluoresence of the detector layer resulting from responses to the movement of test compounds through the porous membrane to the detector layer.

Detection of bioactivity may be determined by a number of methods known in the art. In a preferred embodiment, detection of bioactivity is determined by cellular imaging of fluorescence. For example, imaging may be conducted of a cell layer on a clear glass substrate. In one embodiment, the detector layer is an undemarcated area of physiologically viable cells growing on a flat culture surface. The cells on this surface may or may not be grown to confluence, may be transformed and/or engineered cells, or directly derived from animal tissues and grown as primary cell culture. In a second embodiment of the method of the invention, the array of test compounds is laid out onto a non-porous substrate (such as thin coverglass or plastic sheet) which is transparent or optically clear. Imaging will be through this surface, and through the cell support membrane lying above. The substrate (FIGS. 4, 10) should be inert and solvent tolerant. For example, borosilicate glass sheets of about 200 microns thickness, which may be further surface-treated to give either hydrophobic or hydrophilic properties as desired. This embodiment is shown in the schematic of FIG. 4. In another embodiment, test compounds are first laid out onto a non-porous transparent substrate, and a dry porous transparent membrane (e.g. Anopore or polyester track-etched membrane) overlaid and attached to the aforesaid substrate. In yet another embodiment, compounds are first applied to a similar porous transparent membrane and this is subsequently attached to the solid transparent substrate. These last two methods are useful to restrict lateral movement of compounds following contact with the fluid and detector layers.

In one embodiment of the invention, the detector layer is a layer of physiologically viable cells cultured on a thin porous membrane. A porous membrane useful in the culture and transfer of cells is a transparent non-absorbent membrane with pores of regular and defined diameter which traverse the membrane directly from the upper to the lower side. A porous sheet suitable for cell growth is a track-etched polyester membrane about 10 microns thick with pores between 0.015 and 5 microns diameter at densities of between 600,000,000 to 400,000 pores/cm$^2$ respectively (Nucleopore® from Corning Costar).

The porous membrane which supports the detector layer, complete with the buffer medium which overlays it, is applied onto the (dry) test array. Buffer medium wets the lower surface of the porous membrane (FIG. 4, 19) and forms a continuous thin film 23 between the array of test compounds 21 and the porous membrane 19. Test compounds diffuse up through the pores to the detector layer above. In one embodiment of the invention the detector layer is a monolayer of physiologically viable cells overlaid with physiological buffer solution. The invention includes the possibility that under some conditions it is desirable to have cells grow processes through the membrane to make direct contact with substances on the test array below, with the use of a membrane having an appropriate pore diameter.

Where a test array is generated as a complex mixture of components, such as from the "teabag" method of combinatorial synthesis, or from cDNA library expression systems, a separation step may first necessary. Separation of test components may be conducted in any number of ways known to the art. In one embodiment, components may be separated by the use of one- or two-dimensional separation techniques in non-denaturing gels. The resulting gels may be used directly as test arrays. Specific separation methods will be tailored to the components involved. Any bioactive compounds from such an array would be identified from identical copies of the original test gel.

Specialized light sources and optics are needed to illuminate and image the fluorescence coming from an area the size of a microtitre plate (96-well plate). Such systems are commercially available (e.g., Imaging Research Inc., St Catherines, Ontario, Canada) and consist of a high-power light source directed through a specialized lens which acts both as a wide-field epi-illuminator and imaging device. Another suitable device would be a scanned laser system similar to that used in the FLIPR plate reader (Molecular Devices Corp., USA).

An illumination system useful in the HDFS device is able to deliver excitation light over an area of at least 8.5 by 13 cm at an intensity sufficient to excite measurable fluorescence from that test field (which in most cases will be physiologically viable cells loaded with fluorescent reporters). The illumination may come from a scanned beam, or be wide-field for simultaneous illumination of the entire area. The wavelength of the excitation light should be in a range useful for exciting the commonly used fluorescent reporters. Most of these can be excited by wavelengths within the range 340 to 640 nm. A laser operating at wavelengths in this range would also be a useful light source for the apparatus. An argon-ion laser, tuned to its principal lasing wavelength of 488 nm is able to excite fluorescence from some of the most useful fluorescent reporters, including several variants of GFP, Fluo-3 and JC-1. The imaging system will collect fluorescent light from the entire test area and bring it to focus onto a sensitive imaging photodetector, such as a cooled CCD camera chip.

The imaging capabilities of the HDFS apparatus will be limited to rather low spatial resolution—changes in fluorescence will be imaged from the entire field of detector layer up to 8 cm by 12.5 cm. When the detector layer comprises physiologically viable cells, individual cells need not be resolved in the image, only the fluorescence signals coming from regions in which cells are present.

The imaging times will vary depending on the responses and parameters being monitored. Signaling responses, for instance changes in the level of free calcium in cellular cytoplasm, may first be seen within seconds or minutes following delivery of test compounds to the detector layer. Such changes can be monitored by changes in the fluorescence properties of specific chemical probes, for instance Fluo-3 or Fura-2 (Molecular Probes Inc., Eugene, Oreg., USA) may be used to report on cytoplasmic free calcium. The way in which these changes develop within cells (time-response profile) is an important diagnostic feature of the signaling processes giving rise to them. Rapid responses are therefore recorded by sequences of images, where the time between images in a sequence is between 0.1 and 30 seconds (depending on the response being screened for). Transcription mediated events may require minutes to hours to develop. Monitoring may be continuous or intermittent. For slow responses, two images can be sufficient to gauge the level of response, the first taken before application of test compounds, the second after a period during which the response is estimated to have reached its maximum extent. For some responses a single image, compared against appropriate control measurements made on the same preparation, can be sufficient to guage the level of a response.

Controls relevant to the parameters being measured can be incorporated into the test arrays, both as a check for cell responsiveness and as co-ordinate markers within the arrays. The detector layer is continuous and undemarcated, but because of the close apposition of the test array to the detector layer, the center point of a response in the detector layer corresponds to a conjugate coordinate in the test array. It is helpful to have compounds in the test array which will generate known responses at known coordinates in the detector layer. Responses at the conjugate coordinates in the detector layer act as controls for the system's response, against which responses of the detector layer to unknown compounds may be compared; the points of response to control substances also act as reference points in the detector layer from which the coordinates of other responses can be mapped. For example, when bioactivity is determined as the ability to alter the level of free calcium in cellular cytoplasm, common calcium-mobilizing agonists such as carbamylcholine or adenosine trisphosphate are included in the test array at known coordinates.

As another example, when a change in the cellular ratio of inherently fluorescent NAD(P)H/FAD is the biological parameter being assayed, metabolic inhibitors such as potassium cyanide, antimycin A or rotenone may be used as control and marker compounds. As a further example, when a change in mitochondrial potential is the biological parameter being assayed, chemical uncouplers such as FCCP (carbonyl cyanide p-trifluoromethoxyphenylhydrazone) or DNP (dinitro-phenol) may be used as control and marker compounds.

In many instances, movement of compounds within a thin fluid layer will be involved in many applications of the screening method of the invention, and a concentration gradient will be established from each test point. Those few compounds in a test array which have bioactivity should be detected as spreading rings of response from the focus point of diffusion, within a field of the detector showing no response. The extent of the response areas (measured over time), compared with those from control substances, will provide an indication of potency and solubility of the compound responsible, and also obviate the need to make serial dilutions of test compounds. Toxic or inhibitory substances may also be determined by causing blank sectors in response rings from known agonists. Inhibitory compounds may be determined by their actions on a (pre-)stimulated detector field. Detection of a bioactive compound may incorporate simple image processing to determine the initiation point of a response, its extent and the behaviour of the signal measured in the detector field, from which information it is possible to estimate the potency/efficacy of that compound.

In a specific embodiment, the potency of a compound can be judged in part from the rate of propagation of the peak response along a radius extending from the centre of initiation of that response, a useful image-processing operation is to calculate the difference between successive adjacent images in a sequence, pixel for pixel, which will effectively give the first derivative of the response in time. The values in the difference images around a responding area of cells indicate the rate of change of the response, and hence indicate potency of the compound that initiates the response. The diameter of the ring of response in the difference images is also useful to estimate potency of the compound relative to a known standard active elsewhere in the detector layer.

Simple image correction algorithms may be applied to the data as it is collected, or at some time thereafter, in order to rectify common instrumental deficiencies. The most common of these is to correct for inhomogeneities in the intensity of excitation illumination across the field of the detector layer. This is simply done by using the apparatus to collect a number of fluorescence images from a suitable uniformly fluorescent specimen, such as a flat plate of fluorecent plastic material of uniform thickness. These images are averaged, digitally low-pass filtered and normalised to an average value of 1. All subsequent fluorescent images collected by the apparatus in the same configuration are then divided by the normalised correction image to remove inhomogeneities in the excitation illumination field. It may also be advantageous to correct for two-dimensional distortions in the arrays as imaged from the responses in the detector layer. For this it is necessary to have regular control compounds in the array of test compounds which give recognizable responses. At least three, but preferably more, widely spaced control points are needed in each array. For example, in testing for calcium responses, ionomycin, ATP or carbachol are all useful control compounds. The true coordinates of these known compounds in the array are then used to calculate a correction transformation to align points in the images of the detector layer with points in the array of compounds.

In specific embodiments, the apparatus and method of the invention are as shown in FIGS. 1–4. FIG. 1 shows a high energy light source 1, either a mercury or xenon arc lamp, light from which is collected and collimated by unit 2, directed through a shutter assembly 3 and passes through a excitation filter-changer 4. A high-quality light guide 5, either of fused quartz or a UV-compatible liquid light guide, directs excitation light into the lensing and epi-illumination optics housed in unit 7. Excitation light emerging from 7 evenly illuminates the horizontal detector layer located in the multi-component assembly labeled 10 and 11.

Further details of this assembly are shown in FIGS. 2a–c, 3, and 4. The assembly comprises two solid layers of which 10 is fixed relative to the stage unit 8 which supports it, while layer 11 is moved vertically downward on guide pins (17 in FIGS. 2a,b,c) to bring test compounds into contact with the detector layer. Vertical movement of 11 is controlled by arm 12 driven by unit 13. Four sprung contacts 14 attached to 12 press upon the frame of layer 11 to drive it downwards as arm 12 descends. A separate drive unit 9 controls position of the stage 8 in the horizontal plane, and also is used to adjust focus by movement along the vertical axis.

Fluorescent light emitted by the detector layer is collected by lensing unit 7, passes through an emission filter-changer 15 and is brought to focus on the photosensitive surface of an imaging detector housed in unit 16.

Specified devices (3, 4, 9, 13, 15, 16) are controlled by a central processing unit 6 which issues commands to, and collects data and status information from the devices attached to it. Collected data (images) can also be analyzed by unit 6, or passed to a subsidiary analysis station (not shown). Unit 6 comprises: central processing unit (Intel Pentium chip, or better), RAM, multi-channel serial input/output cards with onboard A/D and D/A converters, one of which cards controls the camera 16 and captures images from it, also a video controller card, VDU, and hard disk memory units.

FIGS. 2a,b,c are schematic diagrams of the test stage, which includes a supporting stage 8 with large rectangular central aperture, the shape and size of which is the same as the area labeled 19. The position of stage 8 is adjusted in the horizontal and vertical axes by the 3-axis positioner 9. These diagrams are drawn for the specific embodiment in which the detector layer is a layer of physiologically viable cells growing on the upper surface of the solid transparent component 10, which also serves to contain the liquid layer 18 which overlays the cells in the detector layer and provides them with necessary nutrients and conditions to keep them alive. The printed array of test compounds 21 is borne on a sheet of track-etched membrane 19 held by a rectangular rigid frame 11. At the beginning of the screening assay, the array 21 is not in contact with the fluid layer 18. The array 21 is held away from the liquid layer by pins 17 which pass through holes 24 in the corners of the frame 11 and which, by friction or "click-stops", prevent it from falling (FIG. 2a). At the appropriate moment, arm 12 is moved down by the drive unit 13 and the four sprung contacts it bears 14 exert pressure on the frame 11 moving it down the guide pins 14 and into the liquid 18 below to a position where it is in very close proximity to the underlying layer of detector cells 20 grown on top of the solid substrate 10 (FIG. 2b). Throughout this procedure, the entire area of the detector layer corresponding to the size and shape of area 19 is illuminated and imaged from below by the additional apparatus shown in FIG. 1.

The apparatus can also be used in a second embodiment of the screening method of the invention, where the test array is laid out on the upper surface of component 10, and components 11 and 19 are a frame and thin transparent track-etched membrane, respectively. In this specific embodiment, the frame 11 is sufficiently deep to contain culture liquid as required to sustain the detector layer of physiologically viable cells growing on the upper surface of the membrane 19.

FIGS. 3 and 4 are schematics to show the relative positions of the different layers in the test-array/detector layers used in the specific embodiments of the invention. FIG. 3 shows the arrangement in which an array of discrete spots of test compounds 21 on a porous membrane 19 is in contact with a liquid layer 18 overlaying the detector layer 20 which is supported by an optically transparent solid substrate 10. The compounds fill the parallel capillary spaces 22 in the track-etched membrane 19. Bioactivity is detected by measuring changes in fluorescence in the detector layer 20 resulting from responses to the movement of test compounds through the porous membrane to the detector layer.

FIG. 4 is a schematic drawing of a second embodiment of the screening method in which a detector layer 20 supported on an optically clear porous membrane 19, and overlaid by a liquid layer 23, is placed onto an optically clear solid substrate 10 bearing an array of test compounds 21. The thin space 18 between components 19 and 10 is filled with solution. This solution is largely transferred as a thin film on the underside of the clear porous membrane, originating from the medium in culture unit (not shown) in which the detector layer has been generated. Some of this solution may also come from 23 having passed through the porous membrane 19. Bioactivity is again detected by measuring changes in fluorescence of the detector layer resulting from responses to the movement of test compounds through the porous membrane to the detector layer.

FIG. 5 is a schematic illustrating the way in which an array of 1536 compounds can be created on a membrane surface, such as would be useful in the first embodiment described above, by simple transfer printing. Compounds are stored in 16 separate 96-well microtitre plates and defined amounts are transferred simultaneously by a 96-pin printing head to the surface 19. The contents of each successive 96-well plate are printed at a slightly offset position, generating an array as shown in FIG. 5b after 4 such printing operations, and a full array of 1536 compounds (FIG. 5c) after 16 printing operations. The holes 24 in frame 11 are used to position and guide the completed array on the pins 17 indicated in FIGS. 2b and 2c. The process illustrated in FIG. 5 can also be used to transfer an array of test compounds to a solid surface such as would be useful for component 10 in the second embodiment of the method described above.

EXAMPLES

Example 1

Screening of Test Compounds for Bioactivity 1,536 test compounds delivered from above were screened with the use of Fluo-3 to measure their effect on the concentration of cytoplasmic free calcium. Test compounds are supplied in a number of 96-well microtitre plates, as is common practice for compounds produced by methods commonly known as conventional or combinatorial chemistry, or for compounds extracted from natural sources. In this example, the compounds are provided in soluble form, and the concentrations and solvents used have previously been tested for compatibility with the apparatus. In this example, 1,536 compounds are tested simultaneously against a known cellular target, specifically a G-protein coupled receptor (GPCR) of the Gq type expressed in a transformed cell line. Gq GPCRs give clearly identifiable changes in intracellular calcium when activated. In order to identify compounds acting on the specific Gq GPCR expressed in the transformed cell line, duplicate experiments are required that use the untransformed cell line as a control "blank" system. This is made particulary easy since the arrays of test compounds are readily duplicated, in a process that is separate and distinct from the actual testing of those compounds for bioactivity.

First, physiologically viable cells are cultured to a near confluent monolayer in a transparent culture dish (10, FIG. 2a–c) in appropriate culture medium and conditions. Immediately prior to being used in the experiment, the cells are loaded with the fluorescent indicator of free cytoplasmic calcium concentration, Fluo-3 (from Molecular Probes, Oregon). This is accomplished by incubating the cells with a 2 to 10 $\mu$M solution of Fluo-3 acetoxymethyl ester (AM) for a period of 10 to 60 minutes, followed by a series of solution exchanges to wash away excess Fluo-3 AM.

The method of transfer of compounds to the track-etched membrane FIGS. 2a–c 19 is illustrated in FIG. 5. In this example, 1,536 compounds are printed as an array 21 on a single track-etched membrane 19, from sixteen individual 96-well microtitre plates in the following manner: A 96-pin printing head is used to transfer defined volumes of compounds (in the range 2 nl to 2 $\mu$l of each compound), one compound per pin, from each 96-well plate in turn (with wash steps between source plates to avoid cross-contamination). Each 96-point print to the membrane occurs in an offset grid, such that 16 print operations are made sequentially on the same membrane and the printed spots of compounds remain discrete and separated from each other (three of these spots are indicated in FIG. 5a, 21). FIG. 5a shows the result of a single 96-point print operation. FIG. 5b after four such operations, and FIG. 5c the finished array after 16 print operations. In this way,just sixteen print operations (and sixteen intermediate wash steps for a single print head) are sufficient to transfer 1,536 compounds to a single test array. The procedure can be readily automated, and multiple copies of each printed sheet made for multiple tests.

Completed arrays are fixed to the pins 17 (FIGS. 2b–c) projecting from the culture dish 10 such that they are supported some small distance above the thin fluid layer 18 covering the physiologically viable cells which form the detector layer. Once the test array is fixed in place over the Fluo-3-loaded cells, the entire assembly is placed onto the test stage as shown in FIG. 2a.

The following events are synchronized by sequential instructions from the computer processing unit 6. First, the test stage is centered over the lensing unit 7 (FIG. 1) and the detector layer it supports is brought into focus by the motor unit 9. Fluo-3 is excited by light of 490 nm, and its fluorescent emissions are collected in the range 505–540 nm. The intensity of emission is increased when the dye binds free calcium. Thus the computer brings a 490 nm band-pass excitation filter into line of the light path coming from units 1 and 2 using the filter changer unit 4. At the same time, a band-pass emission filter for the range 505–540 nm is positioned in the imaging path by unit 15. The shutter 3 is opened for a predetermined exposure period (typically 50 to 500 milliseconds), and during this time the whole area of the detector layer is illuminated with 490 nm light. Fluorescent emission from the Fluo-3 in the cells is collected by the lens 7 and focused into the camera. The camera captures the image and sends it to the processing unit 6 where it is stored and displayed. At regular intervals thereafter, images are captured in sequence by repeatedly opening the shutter 3. Intervals between successive images are typically in the range 0.5 to 30 seconds, depending on the speed of the response expected. Intervals of 0.5 to 2 seconds are usual and sufficient to sample the dynamics of most changes in cellular free calcium. At a predetermined time during this continuing sequence of images, the test array is pushed down the guide pins 17 by the actuating arm 12 and its sprung contacts 14, driven by unit 13. As the test array comes into focus, it is possible at this time to identify compounds which in themselves have fluorescent properties. Such-compounds in the array can be identified, and "false" responses from them in the subsequent images of the detector array either discounted from the final analysis, or be corrected using the initial pre-response value of fluorescence emission recorded in these preliminary images.

In close apposition to the cells in the detector layer, the test array begins to release the compounds it carries. The compounds dissolve into the liquid layer, and fall vertically downwards onto the cells below. Because there is only a thin liquid layer between the membrane of the test array and the cells below, there is insignificant intermixing of adjacent test compounds. If a test compound activates cells below it bearing Gq GPCRs, these cells will respond with an immediate increase in free cytoplasmic calcium, and the fluorescence signal from the Fluo-3 dye they contain will increase. The sequence of images collected during the period of the response (which is typically of 10 seconds to 10 minutes duration) will reveal which cells have so responded, and their position in the area of the detector layer will be correlated with the identity of the compound in the array above. An analysis of the entire area of each image in the sequence, performed on-line by the processing unit 6, yields the following information: the identity of any compound eliciting a response and the maximum amplitude and profile of the response with time, and in the two-dimensional space of the detector layer together with the responses of appropriately chosen standards. From this combined information the potency and efficacy of a test compound can be estimated. Efficacy relative to the standard can be determined from the relative amplitude of the maximal response, and potency may similarly determined from the relative rate of progression of the peak response along a radius emanating from the point of initiation. The final diameter of a response ring may also indicate potency of a compound relative to a control response. Relative potency estimates require that relative amounts of test and control compounds are similar, and that solubilities are not limiting. The use of standard compounds at known points in the array also provides a general control for the experiment, and helps to identify coordinates in the detector layer from which other responses can be mapped.

At the end of the screening assay, the collection of images is stopped, the actuating arm 12 raised, and the test assembly removed. The next assembly is then moved in and the sequence begun afresh. Assembling the test units and exchanging them on the test stage can be automated by appropriate robotic control (not shown in the diagrams).

One of the advantages of the method of the invention is that the method does not require that either the components of the detector layer (e.g. physiologically viable cells), or the different test compounds, be isolated from one another within discrete chambers or compartments, as is common to all high throughput screening procedures currently in use or development. The method also removes the need to dispense microvolumes of test compounds during the period of the assay itself. Delivery of test compounds to detector layers is either by direct contact or by simple movement across thin liquid films. By these methods, delivery and detection becomes a massively parallel process.

Example 2

Screening of Test Compounds for Bioactivity 6,144 compounds delivered from below were screened with the use of JC-1 to measure mitochondrial potential. Mitochondrial potential can be monitored in intact physiologically viable cells using the fluorescent carbocyanine dye JC-1 (5,5',6,6'-tetraethylbenzimidazolylcarbocyanine iodide; Molecular Probes, Inc., Eugene, Oreg., USA).

First, physiologically viable living cells are cultured to a near confluent monolayer on a transparent porous membrane (19, FIG. 4), such as the polyester membrane used in Clear Transwell culture plates (Corning Costar), in appropriate culture medium and conditions. Immediately prior to being used in the experiment, the cells are loaded with the fluorescent indicator JC-1. This is accomplished by incubating the cells with a 2 to 10 $\mu$M solution of JC-1 in a Hepes-buffered modified Krebs-Ringer Solution (KRW) (containing in mM: NaCl 140, KCl 3.6, $NaHCO_3$ 2.0, $CaCl_2$ 1.5, $MgSO_4$ 0.5, $NaH_2PO_4$ 0.5, Hepes 10, D-glucose 5) plus 10% fetal calf serum, at 37° C. for a period of 10 to 60 minutes, followed by a series of solution exchanges to wash away excess JC-1.

The method of transfer of compounds to the transparent substrate (10, FIG. 4) is similar to the method illustrated in FIG. 5. In this example, 6,144 compounds are printed as an array 21 on a single transparent substrate (10, FIG. 4), from 64 individual 96-well microtitre plates in the following manner: A 96-pin printing head is used to transfer defined volumes of compounds (in the range 2 nl to 2 $\mu$l of each compound), one compound per pin, from each 96-well plate in turn (with wash steps between source plates to avoid cross-contamination). Each 96-point print to the membrane occurs in an offset grid, such that 64 print operations are made sequentially on the same membrane and the printed spots of compounds remain discrete and separated from each other (three such spots are indicated in FIG. 5*a*, 21). FIG. 5*a* shows the result of a single 96-point print operation, FIG. 5*b* after four such operations, and FIG. 5*c* the after 16 print operations. In this way, 64 print operations (and 64 intermediate wash steps for a single print head) are sufficient to transfer 6,144 compounds to a single test array. The procedure can be readily automated, and multiple copies of each printed sheet made for multiple tests.

Each completed test array forms the base of an assembly to which is fixed the transparent porous membrane layer, which bears the detector layer of JC-1 loaded cells, in a manner similar to that shown in FIGS. 2*a*–*c*. The detector layer of cells (20, FIG. 4) plus its supporting membrane are supported by a frame similar to 11 in FIG. 2*a*–*c* which fits over the pins 17 (FIGS. 2*b*–*c*) projecting from the test array 10 (FIG. 4) such that they are supported some small distance above 10. The cells in the detector layer are overlaid by a thin fluid layer (23, FIG. 4), and contact a thin fluid layer (18, FIG. 4) on the underside of the porous membrane that is carried over from the medium in their original culture dish (not shown, but similar to the system used in Clear Transwell culture dishes from Corning Costar). In this way the cells of the detector layer are surrounded by and in contact with thin layers, or films, of liquid medium on both sides. The entire assembly is then placed onto the test stage (8) as shown in FIG. 2*a*.

JC-1 is excited by light of 488 nm, and its fluorescent emissions are collected in the range 515 to 545 nm (green), and also in the range 575 to 625 nm (red). The intensity of emissions change in an opposite sense in each of these ranges for any particular response, so that a decrease in mitochondrial potential is signaled by a drop in the red emission, and a simultaneous rise in the green emission. Increase in mitochondrial potential is signaled by increase and decrease in red and green signals respectively. The ratio (red/green) is a useful measure of mitochondrial potential, and corrects for any bleaching of the dye that occurs with cumulative exposure to the excitation light. It can be sufficient, if desired, to collect only one emission range, for which the green is generally preferred.

The following events are synchronized by sequential instructions from the computer processing unit 6. The computer brings a 488 nm band-pass excitation filter into line of the light path coming from units 1 and 2 using the filter changer unit 4. At the same time, a band-pass emission filter for the range 515 to 545 nm is positioned in the imaging path by unit 15. The shutter 3 is opened for a pre-determined exposure period (typically 50 to 500 milliseconds). Fluorescent emission is collected by the lens 7 and focused into the camera. The camera captures the image and sends it to the processing unit 6 where it is displayed. The process is then repeated (if a ratio signal is required) with a second emission filter for the range 575 to 625 nm positioned in the imaging path by unit 15. At regular intervals thereafter, pairs of images are captured in sequence by repeatedly opening the shutter 3 and exchanging emission filters between images.

Having started preliminary imaging, the test stage is centered over the lensing unit 7 (FIG. 1) and the test array it supports is brought into focus by the motor unit 9. As the test array comes into focus, it is possible at this time to identify compounds which in themselves have fluorescent properties. Such compounds in the array can be identified, and "false" responses from them in the subsequent images of the detector array either be discounted from the final analysis, or be corrected using the initial pre-response value of fluorescence emission recorded in these preliminary images.

Focus is then shifted to a predetermined plane about 50 to 300 $\mu$m above the test array, in readiness for the arrival of the detector layer at this position. Once preliminary setup is completed, the experiment is run, and images stored as they are collected. Intervals between successive images are typically in the range 0.5 to 60 seconds, depending on the speed of the response expected. Intervals of 5 to 20 seconds are usual and sufficient to sample the dynamics of most changes in mitochondrial potential. At a predetermined time during this continuing sequence of images, the detector layer and its frame are pushed down the guide pins 17 by the actuating arm 12 and its sprung contacts 14, driven by unit 13. In close apposition to the cells in the detector layer, the test array begins to release the compounds it carries. The compounds dissolve into the liquid layer (18, FIG. 4), and these move up to and first contact any cellular projections that may have grown through the pores of the supporting membrane (19, FIG. 4). Because there is only a thin liquid layer, typically in the range 100 to 500 $\mu$m, between the test array and the porous membrane above, there is rapid contact of compounds with cellular protrusions, and insignificant intermixing of adjacent test compounds. Dissolved compounds then move through the pores of the supporting membrane and into the liquid layer (23) overlaying the cells in the detector layer, and contact the cells from the upper surface.

If a test compound affects mitochondrial potential in the cells it contacts, the JC-1 emissions will change in the manner described. The sequence of images collected during the period of the response (which is typically of 5 to 15 minutes duration) will reveal which cells have so responded, and their position in the area of the detector layer will be correlated with the identity of the compound in the test array below. An analysis of the entire area of each image in the sequence, performed on-line by the processing unit 6, yields the following information: the identity of the compound eliciting the response, the profile of the response with time, the intensity of the response, and also the potency of the compound with reference to a chosen standard. From this combined information the potency and efficacy of a test compound can be estimated. Efficacy relative to the standard can be determined from the relative amplitude of the maximal response, and potency may similarly determined from the relative rate of progression of the peak response along a radius emanating from the point of initiation. The final diameter of a response ring may also indicate potency of a compound relative to a control response. Relative potency estimates require that relative amounts of test and control compounds are similar, and that solubilities are not limiting. The use of standard compounds at known points in the array also provides a general control for the experiment, and helps to identify coordinates in the detector layer from which other responses can be mapped.

At the end of the screening assay, the sequence collection of images is stopped, the actuating arm 12 raised, and the test assembly removed. The next assembly is then moved in and the sequence begun afresh. Assembling the test units and exchanging them on the test stage can be automated by appropriate robotic control (not shown in the diagrams).

Example 3

Screening of Test Compounds with Fluo-3

6,144 test compounds delivered from above were screened with Fluo-3 for the effect on the concentration of cytoplasmic free calcium and a modified FLIPR devise was used as part of the apparatus to illuminate and image the detector layer and its responses. Physiologically viable living cells are cultured to a near confluent monolayer in a transparent culture dish (10, FIGS. 2a–c) in appropriate culture medium and conditions. Immediately prior to being used in the experiment, the cells are loaded with the fluorescent indicator of free cytoplasmic calcium concentration, Fluo-3. This is accomplished by incubating the cells with a 2 to 10 $\mu$M solution of Fluo-3 acetoxymethyl ester (AM) for a period of 10 to 60 minutes, followed by a series of solution exchanges to wash away excess Fluo-3 AM.

The method of transfer of compounds to the track-etched membrane FIGS. 2a–c 19 is illustrated in FIG. 5. In this example, 6,144 compounds are printed as an array 21 on a single track-etched membrane 19, from 64 individual 96-well microtitre plates in the following manner: A 96-pin printing head is used to transfer defined volumes of compounds (in the range 2 nl to 2 $\mu$l of each compound), one compound per pin, from each 96-well plate in turn (with wash steps between source plates to avoid cross-contamination). Each 96-point print to the membrane occurs in an offset grid, such that 64 print operations are made sequentially on the same membrane and the printed spots of compounds remain discrete and separated from each other (three of these spots are indicated in FIG. 5a, 21). FIG. 5a shows the result of a single 96-point print operation, FIG. 5b after four such operations, and FIG. 5c the array after 16 print operations. In this way, just 64 print operations (and 64 intermediate wash steps for a single print head) are sufficient to transfer 6,144 compounds to a single test array. The procedure can be readily automated, and multiple copies of each printed sheet made for multiple tests.

Completed arrays are fixed to the pins 17 (FIGS. 2b–c) projecting from the culture dish 10 such that they are supported some small distance above the thin fluid layer 18 covering the physiologically viable cells which form the detector layer. Once the test array is fixed in place over the Fluo-3-loaded cells, the entire assembly is placed onto the test stage as shown in FIG. 2a.

The following events are synchronized by sequential instructions from the computer processing unit 6. First, the test stage is centered over the lensing unit 7 (FIG. 1) and the detector layer it supports is brought into focus by the motor unit 9. Fluo-3 is excited by light of 488 nm, and its fluorescent emissions are collected in the range 505–540 nm. The intensity of emission is increased when the dye binds free calcium. In this embodiment, the illumination and optical detection system in use is a modified version of a commercially available fluorescence imaging plate reader (FLIPR from Molecular Devices Corp., USA). The computer opens a shutter to allow light from a 10 watt argon-ion laser, run at about 1 watt emission intensity, to contact a rapidly rotating prismatic reflector, or scanning head, which in combination with appropriate expansion and focusing lenses and static mirrors causes the laser light to completely illuminate the area of the detector layer from below. This scanning illumination system (not shown) replaces components 1 to 5 in FIG. 1. The area of the detector layer is imaged from below using a smaller and simpler version of the lens shown as 7 in FIG. 1, together with a number of stationary plane mirrors positioned appropriately (not shown).

A band-pass emission filter for the range 505–540 nm is positioned in the imaging path by unit 15. The shutter in front of the laser beam is opened for a pre-determined exposure period (typically 50 to 1000 milliseconds), and during this time the whole area of the detector layer is raster-scanned with 488 nm light. Fluorescent emission from the Fluo-3 in the cells is collected by the lens 7 and focused into the camera. The camera captures the image and sends it to the processing unit 6 where it is stored and displayed. At regular intervals thereafter, images are captured in sequence by repeatedly opening the shutter 3. Intervals between successive images are typically in the range 0.5 to 30 seconds, depending on the speed of the response expected. Intervals of 0.5 to 2 seconds are usual and sufficient to sample the dynamics of most changes in cellular free calcium. At a predetermined time during this continuing sequence of images, the test array is pushed down the guide pins 17 by the actuating arm 12 and its sprung contacts 14, driven by unit 13. As the test-array comes into focus, it is possible at this time to identify compounds which in themselves have fluorescent properties. Such compounds in the array can be identified, and "false" responses from them in the subsequent images of the detector array either be discounted from the final analysis, or be corrected using the initial pre-response value of fluorescence emission recorded in these preliminary images.

In close apposition to the cells in the detector layer, the test array begins to release the compounds it carries. The compounds dissolve into the liquid layer, and fall vertically downwards onto the cells below. Because there is only a thin liquid layer between the membrane of the test array and the cells below, there is insignificant intermixing of adjacent test compounds. If a test compound activates cells below it bearing Gq GPCRs, these cells will respond with an immediate increase in free cytoplasmic calcium, and the fluorescence signal from the Fluo-3 dye they contain will increase. The sequence of images collected during the period of the response (which is typically of 10 seconds to 10 minutes duration) will reveal which cells have so responded, and their position in the area of the detector layer will be correlated with the identity of the compound in the array above. An analysis of the entire area of each image in the sequence, performed on-line by the processing unit 6, yields the following information: the identity of the compound eliciting the response, the profile of the response with time, the intensity of the response, and also the potency of the compound with reference to a chosen standard. From this combined information the potency and efficacy of a test compound can be estimated. Efficacy relative to the standard can be determined from the relative amplitude of the maximal response, and potency may similarly determined from the relative rate of progression of the peak response along a radius emanating from the point of initiation. The final diameter of a response ring may also indicate potency of a compound relative to a control response. Relative potency estimates require that relative amounts of test and control compounds are similar, and that solubilities are not limiting. The use of standard compounds at known points in the array also provides a general control for the experiment, and helps to identify coordinates in the detector layer from which other responses can be mapped.

At the end of the screening assay, the collection of images is stopped, the actuating arm 12 raised, and the test assembly removed. The next assembly is then moved in and the sequence begun afresh. Assembling the test units and exchanging them on the test stage can be automated by appropriate robotic control (not shown in the diagrams).

Example 4

Screening of Test Compounds with GFP-fusion 6,144 test compounds delivered from below were screened for bioactivity with the use of an intermediary porous membrane to apply the test array of compounds, use of a modified FLIPR device as part of the apparatus to illuminate and image the detector layer, and use of a GFP-fusion to report on the response of the cells in the detector layer. The compounds are tested for ability to affect the level of the second messenger cAMP in physiologically viable cells. Changes in cAMP can be monitored using a genetically encoded fusion protein between a variant of the green fluorescent protein (GFP) and the catalytic subunit of cAMP-dependent protein kinase, cAK; this fusion protein probe is referred to hereafter as C-GFP$^{LT}$.

First, physiologically viable living cells stably or transiently transfected with the C-GFP$^{LT}$ probe are cultured to a near confluent monolayer on a transparent porous membrane (19, FIG. 4), such as the polyester membrane used in Clear Transwell culture plates (Corning Costar), in appropriate culture medium and conditions. Immediately prior to being used in the experiment, the cells are washed in a Hepes-buffered modified Krebs-Ringer Solution (KRW) (containing in mM: NaCl 140, KCl 3.6, NaHCO$_3$ 2.0, CaCl$_2$ 1.5, MgSO$_4$ 0.5, NaH$_2$PO$_4$ 0.5, Hepes 10, D-glucose 5), at 37° C. to remove cell-culture medium, which can increase background fluorescence due to autofluorescence from flavinoid compounds therein.

The two possible methods of transfer of compounds from below in this embodiment are different to that described in Example 2. In one embodiment the compounds are applied directly to a transparent porous membrane, such as Anopore membrane (Whatman International Ltd.) or a clear polyester track-etched membrane (as in Clear Transwells, from Corning Costar), and this porous membrane is then fixed to the transparent substrate (10, FIG. 4). In a second embodiment, compounds are transferred directly to the solid transparent substrate, as in Example 2, but then a transparent porous membrane is overlaid and fixed in place. The presence of the additional porous transparent membrane in each of these embodiments is useful to confine lateral movement of compounds once they are contacted with the liquid layer (18, FIG. 4). The method of transfer of 6,144 compounds to membrane or transparent substrate is similar to the method illustrated in FIG. 5.

Each completed test array (solid transparent substrate plus transparent porous membrane, fixed together as described)

forms the base of an assembly to which is fixed the transparent porous membrane layer which bears the detector layer of C-GFP$^{LT}$-expressing cells, in a manner similar to that shown in FIGS. 2a–c. The detector layer of cells (20, FIG. 4) plus its supporting membrane is supported by the a frame similar to 11 in FIGS. 2a–c which fits over the pins 17 (FIGS. 2b–c) projecting from the test array 10 (FIG. 4) such that they are supported some small distance above 10. The cells in the detector layer are overlaid by a thin fluid layer (23, FIG. 4), and contact a thin fluid layer (18, FIG. 4) on the underside of the porous membrane that is carried over from the medium in their original culture dish (not shown, but similar to the system used in Clear Transwell culture dishes from Corning Costar). In this way the cells of the detector layer are surrounded by and in contact with liquid medium on both sides. The entire assembly is then placed onto the test stage (8) as shown in FIG. 2a.

The following events are synchronized by sequential instructions from the computer processing unit 6. GFP$^{LT}$ is excited by light of 488 nm, and its fluorescent emissions are collected in the range 500–540 nm. In this embodiment, the illumination and optical detection system in use is a modified version of a commercially available fluorescence imaging plate reader (FLIPR from Molecular Devices Corp., USA). The computer opens a shutter to allow light from a 10 watt argon-ion laser, run at an emission intensity of about 1 watt, to contact a rapidly rotating prismatic reflector, or scanning head, which in combination with appropriate expansion and focusing lenses and static mirrors causes the laser light to completely illuminate an area equivalent to that of the detector layer from below. This scanning illumination system (not shown) replaces components 1 to 5 in FIG. 1. The area of the detector layer is imaged from below using a smaller and simpler version of the lens shown as 7 in FIG. 1, together with a number of stationary plane mirrors positioned appropriately (not shown).

A band-pass emission filter for the range 500–540 nm is positioned in the imaging path by unit 15. The shutter in front of the laser beam is opened for a pre-determined exposure period (typically 50 to 1000 milliseconds), and during this time the whole area of the detector layer is raster-scanned with 488 nm light.

The test stage is centered over the lensing unit 7 (FIG. 1) and the detector layer it supports is brought into focus by the motor unit 9. As the test array comes into focus, it is possible at this time to identify compounds which in themselves have fluorescent properties. Such compounds in the array can be identified, and "false" responses from them in the subsequent images of the detector array either be discounted from the final analysis, or be corrected using the initial pre-response value of fluorescence emission recorded in these preliminary images. Focus is then shifted to a predetermined plane about 50 to 300 $\mu$m above the test array, in readiness for the arrival of the detector layer at this position.

Fluorescent emission from GFP$^{LT}$ in the cells is collected by the lens 7 and focused into the camera. The camera captures the image and sends it to the processing unit 6 where it is stored and displayed. At regular intervals thereafter, images are captured in sequence by repeatedly opening the shutter 3. Intervals between successive images are typically in the range 5 to 30 seconds, depending on the speed of the response expected. Intervals of 10 to 15 seconds are usual and sufficient to sample the dynamics of most changes in C-GFP$^{LT}$ redistribution. At a predetermined time during this continuing sequence of images, the detector layer and its frame are pushed down the guide pins 17 by the actuating arm 12 and its sprung contacts 14, driven by unit 13. In close apposition to the cells in the detector layer, the test array begins to release the compounds it carries. The compounds dissolve into the liquid layer (18, FIG. 4), and these move up to and first contact any cellular projections that may have grown through the pores of the supporting membrane (19, FIG. 4). Because there is only a thin liquid layer, typically in the range 100 to 500 $\mu$m, between the test array and the porous membrane above, there is rapid contact of compounds with cellular protrusions, and insignificant intermixing of adjacent test compounds. Dissolved compounds then move through the pores of the supporting membrane and into the liquid layer (23) overlaying the cells in the detector layer, and contact the cells from the upper surface.

If a test compound affects levels of cAMP in the cells it contacts, C-GFP$^{LT}$ changes it distribution within the cells, and the fluorescence signal within the image of the detector layer registers this change in distribution. The sequence of images collected during the period of the response (which is typically of 5 to 15 minutes duration) will reveal which cells have so responded, and their position in the area of the detector layer will be correlated with the identity of the compound in the test array below. An analysis of the entire area of each image in the sequence, performed on-line by the processing unit 6, yields the following information: the identity of the compound eliciting the response, the profile of the response with time, the intensity of the response, and also the potency of the compound with reference to a chosen standard. From this combined information the potency and efficacy of a test compound can be estimated. Efficacy relative to the standard can be determined from the relative amplitude of the maximal response, and potency may similarly determined from the relative rate of progression of the peak response along a radius emanating from the point of initiation. The final diameter of a response ring may also indicate potency of a compound relative to a control response. Relative potency estimates require that relative amounts of test and control compounds are similar, and that solubilities are not limiting. The use of standard compounds at known points in the array also provides a general control for the experiment, and helps to identify coordinates in the detector layer from which other responses can be mapped.

At the end of the screening assay, the collection of images is stopped, the actuating arm 12 raised, and the test assembly removed. The next assembly is then moved in and the sequence begun afresh. Assembling the test units and exchanging them on the test stage can be automated by appropriate robotic control (not shown in the diagrams).

Example 5

Screening of Test Compounds with GFP-fusion.

1,536 test compounds delivered from above were screened for bioactivity with the use of a modified FLIPR device as part of the apparatus to illuminate and image the detector layer, and use of a GFP-fusion with a permeabilisation technique to report on the response of the cells in the detector layer. The compounds were tested for ability to affect the level of the second messenger cAMP in physiologically viable cells.

First, physiologically viable living cells stably or transiently transfected with the C-GFP$^{LT}$ probe are cultured to a near confluent monolayer on a transparent substrate (10, FIG. 3), such as thin (less than 1 mm thickness) tissue culture-treated glass or plastic, in appropriate culture medium and conditions. Immediately prior to being used in the experiment, the cells are washed in a Hepes-buffered modified Krebs-Ringer Solution (KRW) (containing in mM: NaCl 140, KCl 3.6, NaHCO$_3$ 2.0, CaCl$_2$ 1.5, MgSO$_4$ 0.5, NaH$_2$PO$_4$ 0.5, Hepes 10, D-glucose 5), at 37° C. to remove cell-culture medium, which can increase background fluorescence due to autofluorescence from flavinoid compounds therein.

The method of transfer of 1,536 compounds to a porous membrane (19, FIG. 3) is illustrated in FIG. 5. Completed arrays are fixed to the pins 17 (FIGS. 2b–c) projecting from the culture dish 10 such that they are supported some small distance above the thin fluid layer 18 covering the physiologically viable C-GFP$^{LT}$-expressing cells which form the detector layer. Once the test array is fixed in place over the C-GFP$^{LT}$-expressing cells, the entire assembly is placed onto the test stage as shown in FIG. 2a.

The following events are synchronized by sequential instructions from the computer processing unit 6. GFP$^{LT}$ is excited by light of 488 nm, and its fluorescent emissions are collected in the range 500–540 nm. In this embodiment, the illumination and optical detection system in use is a modified version of a commercially available fluorescence imaging plate reader (FLIPR from Molecular Devices Corp., USA). The computer opens a shutter to allow light from a 10 watt argon-ion laser, run at about 1 watt emission intensity, to contact a rapidly rotating prismatic reflector, or scanning head, which in combination with appropriate expansion and focusing lenses and static mirrors causes the laser light to completely illuminate the area of the detector layer from below. This scanning illumination system (not shown) replaces components 1 to 5 in FIG. 1. The area of the detector layer is imaged from below using a smaller and simpler version of the lens shown as 7 in FIG. 1, together with a number of stationary plane mirrors positioned appropriately (not shown).

A band-pass emission filter for the range 500–540 nm is positioned in the imaging path by unit 15. The shutter in front of the laser beam is opened for a predetermined exposure period (typically 50 to 1000 milliseconds), and during this time the whole area of the detector layer is raster-scanned with 488 nm light.

The test stage is centered over the lensing unit 7 (FIG. 1) and the detector layer it supports is brought into focus by the motor unit 9. Fluorescent emission from GFP$^{LT}$ in the cells is collected by the lens 7 and focused into the camera. The camera captures the image and sends it to the processing unit 6 where it is stored and displayed. At regular intervals thereafter, images are captured in sequence by repeatedly opening the shutter 3. In this embodiment, a number of images are captured at the start of the experiment to sample the initial distribution of fluorescence in the detector layer, then the test array and its frame are pushed down the guide pins 17 by the actuating arm 12 and its sprung contacts 14, driven by unit 13. As the test array comes into focus, it is possible at this time to identify compounds which in themselves have fluorescent properties. Such compounds in the array can be identified, and "false" responses from them in the subsequent images of the detector array either be discounted from the final analysis, or be corrected using the initial pre-response value of fluorescence emission recorded in these preliminary images.

In close apposition to the cells in the detector layer, the test array begins to release the compounds it carries. The compounds dissolve into the liquid layer (18, FIG. 3), and fall vertically downwards onto the cells below. Because there is only a thin liquid layer between the membrane of the test array and the cells below, there is insignificant intermixing of adjacent test compounds.

If a test compound affects levels of cAMP in the cells it contacts, C-GFP$^{LT}$ changes it distribution and mobility within the cells. The cells in the detector layer can now be permeabilised with agents such as TritonX-100 so that mobile C-GFP$^{LT}$ can be washed out of the cells. This is done after a period of 2 to 10 minutes following application of the array of test compounds to the detector layer: the test array is removed from its position above the detector layer of cells, and the thin layer of fluid (18, FIG. 3) rapidly replaced with KRW buffer containing no calcium, but including an agent which will permeabilise the plasma membrane of the cells in the detector layer, for example 0.01% TritonX-100. After a short period of time, from 30 seconds to 10 minutes, the buffer is exchanged to wash away C-GFP$^{LT}$ that has been released from the cells, and another series of images is collected as before. These images will reveal which cells have responded, and their position in the area of the detector layer will be correlated with the identity of the compound in the test array below. An analysis of the entire area of each image in the sequence, performed on-line by the processing unit 6, yields the following information: the identity of the compound eliciting the response, the profile of the response with time, the intensity of the response, and also the potency of the compound with reference to a chosen standard. From this combined information the potency and efficacy of a test compound can be estimated. Efficacy relative to the standard can be determined from the relative amplitude of the maximal response, and potency may similarly determined from the relative rate of progression of the peak response along a radius emanating from the point of initiation. The final diameter of a response compared directly to a known standard which is included in the array at known points ring may also indicate potency of a compound relative to a control response. Relative potency estimates require that relative amounts of test and control compounds are similar, and that solubilities are not limiting. The use of standard compounds at known points in the array also provides a general control for the experiment, and helps to identify coordinates in the detector layer from which other responses can be mapped.

At the end of the screening assay, the collection of images is stopped, the actuating arm 12 raised, and the test assembly removed. The next assembly is then moved in and the sequence begun afresh. Assembling the test units and exchanging them on the test stage can be automated by appropriate robotic control (not shown in the diagrams).

Example 6

Screening of Test Compounds with the use of an Intermediary Material and Inverted Apparatus.

6,144 test compounds delivered from below were screened for bioactivity with the use of an intermediary material to carry the test array of compounds and their effect on cencentration of cytoplasmic free calcium were measured using an inverted form of the apparatus to image from above to accomodate non-transparent materials as matrix for the test array. The compounds were tested against a G-protein coupled receptor (GPCR) of the Gq type expressed in a transformed cell line. Gq GPCRs give clearly identifiable changes in intracellular calcium when activated.

First, physiologically viable living cells are cultured to a near confluent monolayer on a transparent porous membrane (19, FIG. 4), such as the polyester membrane used in Clear Transwell culture plates (Corning Costar), in appropriate culture medium and conditions. Immediately prior to being used in the experiment, the cells are loaded with the fluorescent indicator of free cytoplasmic calcium concentration, Fluo-3 (from Molecular Probes, Oregon). This is accomplished by incubating the cells with a 2 to 10 µM solution of Fluo-3 acetoxymethyl ester (AM) in a Hepes-buffered modified Krebs-Ringer Solution (KRW) (containing in mM: NaCl 140, KCl 3.6. NaHCO$_3$ 2.0, CaCl$_2$ 1.5, MgSO$_4$ 0.5, NaH$_2$PO$_4$ 0.5, Hepes 10, D-glucose 5), at 37° C. for a period of 10 to 60 minutes, followed by a series of solution exchanges to wash away excess Fluo-3 AM.

In this embodiment the compounds are fixed to an opaque or semi-transparent carrier material, which may be an absorbent cast-cellulosic membrane, or a gel matrix, or any material capable of transferring the compounds of interest in the application. The compounds of the test array may be fixed in a more or less permanent manner to the substance of the transfer material, such as by covalent or other chemical bonds. The method of transfer of 6,144 compounds to the carrier material may be similar to the method illustrated in FIG. 5, and described in Example 2, or may involve chemical synthesis on the transfer material itself. The transfer material, and the test array it carries, is then fixed to a solid substrate 10 FIG. 4.

Each completed test array (solid substrate plus carrier material, fixed together as described) forms the base of an assembly to which is fixed the transparent porous membrane layer which bears the detector layer of cells, in a manner similar to that shown in FIGS. 2a–c (for the embodiment described in Example 1). The detector layer of cells (20, FIG. 4) plus its supporting membrane is supported by the a frame similar to 11 in FIGS. 2a–c which fits over the pins 17 (FIGS. 2b–c) projecting from the test array 10 (FIG. 4) such that they are supported some small distance above 10. The cells in the detector layer are overlaid by a thin fluid layer (23, FIG. 4), and contact a thin fluid layer (18, FIG. 4) on the underside of the porous membrane that is carried over from the medium in their original culture dish (not shown, but similar to the system used in Clear Transwell culture dishes from Corning Costar). In this way the cells of the detector layer are surrounded by and in contact with liquid medium on both sides. The entire assembly is then placed onto the test stage (8) as shown in FIG. 2a.

In this embodiment, the detector layer is illuminated and imaged from above, thus the elements 1 through 5 and 7, 15 and 16 are inverted so as to lie in proper correspondence to one another above the test assembly and stage (8 through 14). The following events are synchronized by sequential instructions from the computer processing unit 6. Fluo-3 is excited by light of 490 nm, and its fluorescent emissions are collected in the range 505–540 nm. The intensity of emission is increased when the dye binds free calcium. Thus the computer brings a 490 nm band-pass excitation filter into line of the light path coming from units 1 and 2 using the filter changer unit 4. At the same time, a band-pass emission filter for the range 505–540 nm is positioned in the imaging path by unit 15. The shutter 3 is opened for a pre-determined exposure period (typically 50 to 500 milliseconds), and during this time an whole area corresponding to that of the detector layer is illuminated with 490 nm light. Fluorescent emission is collected by the lens 7 and focused into the camera The camera captures each image and sends it to the processing unit 6 where it is displayed, and may be stored.

The test stage is centered below a lensing unit 7 (similar to FIG. 1) and the detector layer it supports is brought into focus by the motor unit 9. As the test array comes into focus, it is possible at this time to identify compounds which in themselves have fluorescent properties. Such compounds in the array can be identified, and "false" responses from them in the subsequent images of the detector array either be discounted from the final analysis, or be corrected using the initial pre-response value of fluorescence emission recorded in these preliminary images. Focus is then shifted to a predetermined plane about 50 to 300 µm above the test array, in readiness for the arrival of the detector layer at this position. At regular intervals thereafter, images are captured in sequence by repeatedly opening the shutter 3. Intervals between successive images are typically in the range 0.5 to 30 seconds, depending on the speed of the response expected. Intervals of 0.5 to 2 seconds are usual and sufficient to sample the dynamics of most changes in cellular free calcium. At a predetermined time during this continuing sequence of images, the detector layer is pushed down the guide pins 17 by the actuating arm 12 and its sprung contacts 14, driven by unit 13. The arm assembly is then lifted and moved out of the field of view of the imaging camera 7.

In close apposition to the cells in the detector layer, the test array begins to release the compounds it carries. The compounds, if soluble, dissolve into the liquid layer (18, FIG. 4), and these move up to and first contact any cellular projections that may have grown through the pores of the supporting membrane (19, FIG. 4). Because there is only a thin liquid layer, typically in the range 100 to 500 µm, between the test array and the porous membrane above, there is rapid contact of compounds with cellular protrusions, and insignificant intermixing of adjacent test compounds. Dissolved compounds then move through the pores of the supporting membrane and into the liquid layer (23) overlaying the cells in the detector layer, and contact the cells from the upper surface. Virtually insoluble compounds, or those linked to the substrate by covalent or other chemical bonds, require that the membrane supporting the detector layer physically contacts the array of test compounds beneath. Cellular processes which traverse the supporting membrane (19, FIG. 4) will then be able to make contact with the test compounds in the array.

If a test compound activates cells via Gq GPCRs, these cells will respond with an immediate increase in free cytoplasmic calcium, and the fluorescence signal from the Fluo-3 dye they contain will increase. The sequence of images collected during the period of the response (which is typically of 10 seconds to 10 minutes duration) will reveal which cells have so responded, and their position in the area of the detector layer will be correlated with the identity of the compound in the array above. An analysis of the entire area of each image in the sequence, performed on-line by the processing unit 6, yields the following information: the identity of any compound eliciting a response and the maximum amplitude and profile of the response with time, and in the two-dimensional space of the detector layer together with the responses of appropriately chosen standards. From this combined information the potency and efficacy of a test compound can be estimated. Efficacy relative to the standard can be determined from the relative amplitude of the maximal response, and potency may similarly determined from the relative rate of progression of the peak response along a radius emanating from the point of initiation. The final diameter of a response ring may also indicate potency of a compound relative to a control response. Relative potency estimates require that relative amounts of test and control compounds are similar, and that solubilities are not limiting. The use of standard compounds at known points in the array also provides a general control for the experiment, and helps to identify coordinates in the detector layer from which other responses can be mapped.

At the end of the screening assay, the collection of images is stopped, and the test assembly removed. The next assembly is then moved in and the sequence begun afresh. Assembling the test units and exchanging them on the test stage can be automated by appropriate robotic control (not shown in the diagrams).

Example 7

Carbamylcholine Response from BHKhM1 Cells Loaded with Fluo-3

Figure 6:
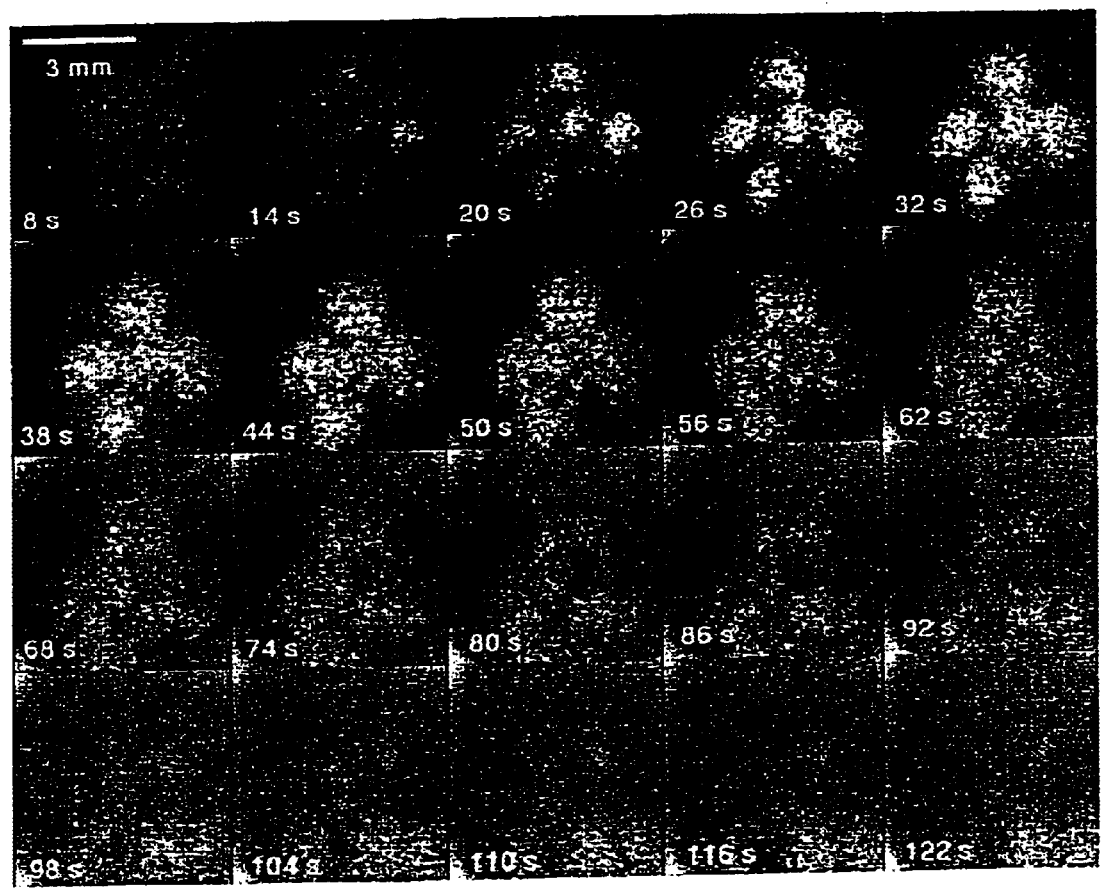
FIGS. 6–7 show the response of fluo-3 loaded BHKhM1 cells to carbamylcholine (Cch) (Example 7). Cells were grown on tissue culture treated polystyrene to near confluence (>90%) in DMEM 10% FCS, 100 $\mu$g/ml streptomycin, 100 IU/ml penicillin and 500 nM methotrexate to maintain the human muscarinic receptor type1 construct.
Figure 7:
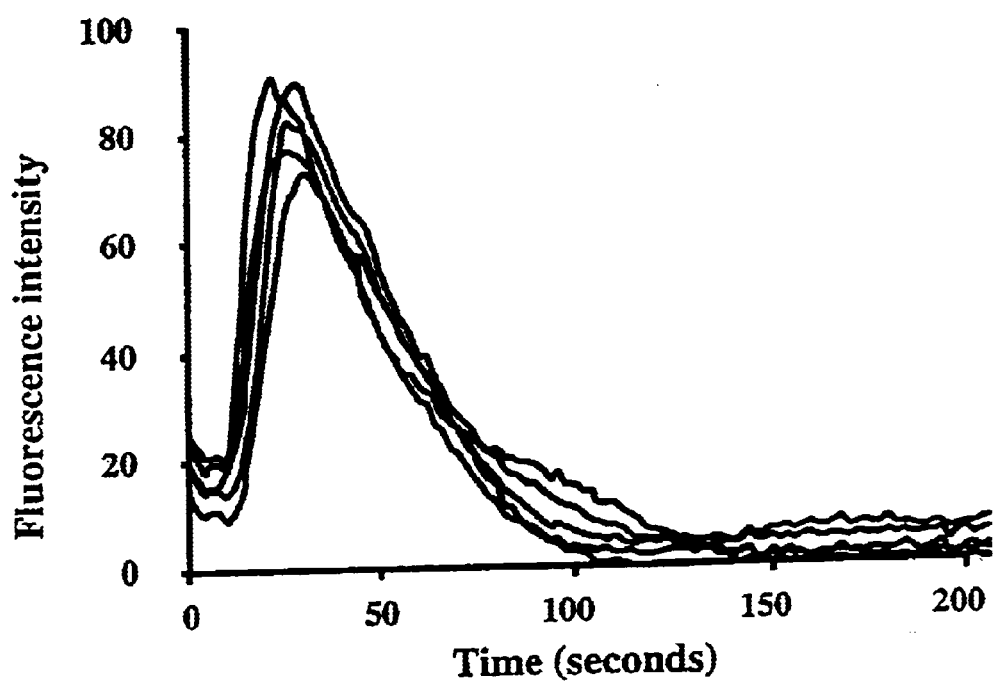

Cells were grown on tissue culture treated polystyrene to near confluence (>90%) in DMEM 10% FCS, 100 µg/ml streptomycin, 100 IU/ml penicillin and 500 nM methotrexate to maintain the human muscarinic receptor type1 construct. The $EC_{50}$ for a carbamylcholine (Cch) $[Ca^{2+}]_i$ response through this receptor is known from previous studies to be about 1 µM. Carbamylcholine (Sigma) was printed as five spots (FIG. 6) with a spacing of about 2 mm onto a supported porous aluminium oxide filter (Anopore, Whatman International Ltd. Maidstone, Kent, UK) as a 1 mM solution in ethanol and allowed to dry. The fluid volume used for each spot is approx. 1 nanoliter. The BHKhM1 cells were loaded with 7 µM Fluo-3 AM (Molecular Probes Inc.) for 50–60 min in the presence of 0.02% Pluronic-127 (Molecular Probes Inc.) in a Hepes-buffered modified Krebs-Ringer Solution (KRW) (containing in mM: NaCl 140, KCl 3.6, $NaHCO_3$ 2.0, $CaCl_2$ 1.5, $MgSO_4$ 0.5, $NaH_2PO_4$ 0.5, Hepes 10, D-glucose 5) at 37° C. After three washes in KRW, the cells were placed on the stage of a Nikon Diaphot epifluorescence microscope and imaged using a 2× plan apochromat objective and a CCD camera (Princeton Instruments, NY, USA). The cells were excited by 450–490 nm light and light emitted from the cells was filtered by a dichroic mirror (505 nm) and an emission filter (510–560 nm). Exposure/integration times of 1.0 s were used and images acquired at 2 s intervals. At a time 0, that is 8 s before the first image in FIG. 6 the filter with spots of carbamylcholine was lowered down into the buffer overlying the cells and rapidly adjusted to a distance of about 300 µm above the cell layer and thereafter fixed in that position. The image series in FIG. 6 shows the initial response to carbamylcholine with a time resolution of 6 s. One can observe how five spots appear at 20–26 s and then slowly spread radially with time and finally fade away. FIG. 7 displays the fluorescence intensity over time from the five spots depicted in FIG. 6. The responses peak after about 30 seconds and then decrease with time toward a baseline level. The entire event is over in about 90 s. All five responses are very uniform in time and shape. This response profile is very similar to those seen previously in the same cell type by other measurement methods (Almholt et al. (1999) Biochem. J. 337:211–218).

Example 8

Mitochondrial Response with A10 Smooth Muscle Cells Loaded with JC-1 to FCCP (a Protonophore/mitochondrial Uncoupler).

Figure 8:
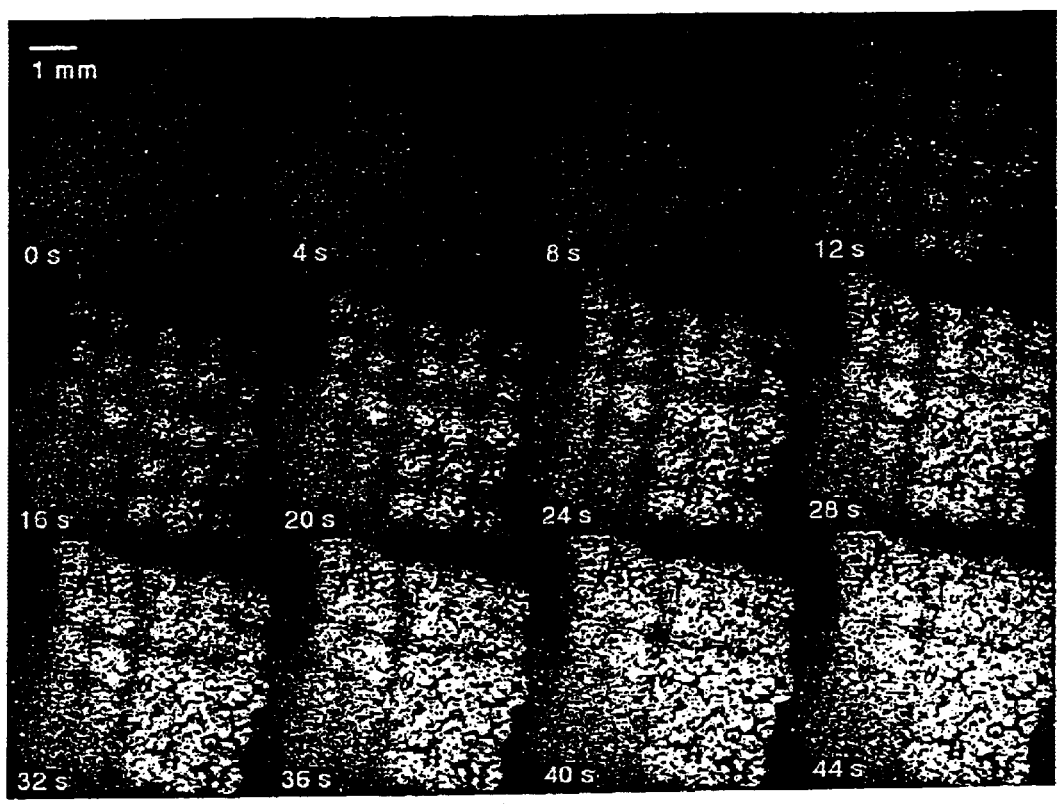
FIGS. 8–11 show the mitochondrial response from two different experiments with A10 smooth muscle cells loaded with JC-1 to FCCP (a protonophore/mitochondrial uncoupler) (Example 8). Cells were grown to confluence on tissue culture treated polystyrene in DMEM 10% FCS, 100 $\mu$g/ml streptomycin and 100 IU/ml penicillin.

Cells were grown to confluence on tissue culture treated polystyrene in DMEM 10% FCS, 100 µg/ml streptomycin and 100 IU/ml penicillin. The $EC_{50}$ for a mitochondrial depolarisation in these cells is known to be about 8 nM. FCCP. FCCP (Sigma) was printed onto a supported porous aluminium oxide filter (Anopore, Whatman International Ltd, Maidstone, Kent, UK) in a 5×5 spot grid, at a single concentration of 50 µM in DMSO, or as five rows of five spots (50, 5, 05, 0.05 and 0.005 µM in DMSO) and allowed to dry. The volume of liquid in each spot was approximately 1 nanoliter. The A10 cells were loaded for 25 min in KRW supplemented with 10% FCS and 5 µM JC-1 (Molecular Probes Inc.) at 37° C. After three washes in KRW, the cells were placed on the stage of a Nikon Diaphot epifluorescence microscope and imaged using a 2× plan apochromatic objective and a CCD camera (Princeton Instruments, NY USA). The cells were excited by 450–490 nm light and light emitted from the cells was filtered by a dichroic mirror (505 nm) and an emission filter (510–560 nm). Exposure/ntegration times of 0.5 s were used and images acquired at 4 s intervals. At the time indicated as 0 in FIGS. 8 and 9 a filter with spots of FCCP in the patterns mentioned above was lowered down into the buffer overlying the cells and rapidly adjusted to a distance of about 300 µm above the cell layer and thereafter fixed in that position. The image series in FIG. 8 shows the response of 25 spots of FCCP at the same concentration. As can be seen the response sectors start out as discrete spots that with time spread over a larger surface. The fluorescence intensity time profile for five central spots are displayed in FIG. 9. A steep rise in fluorescence intensity, indicative of mitochondrial membrane depolarisation, can be observed with a short lag phase (10–15 s). The rise is followed by a sustained increase throughout the course of the experiment.

Figure 9:
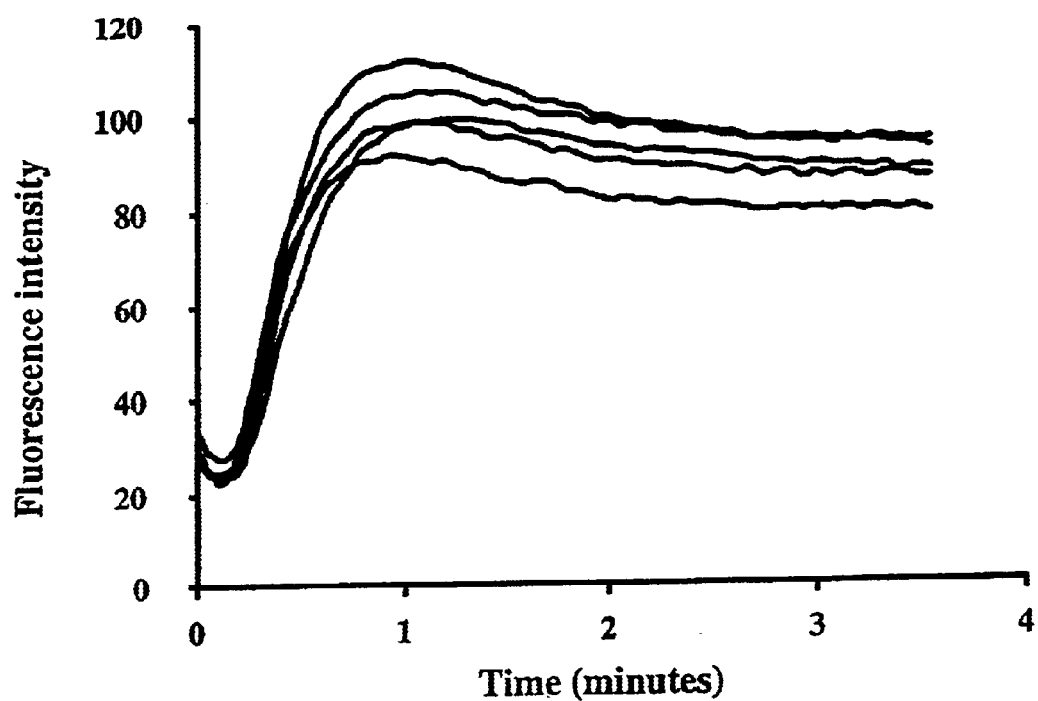
Figure 10:
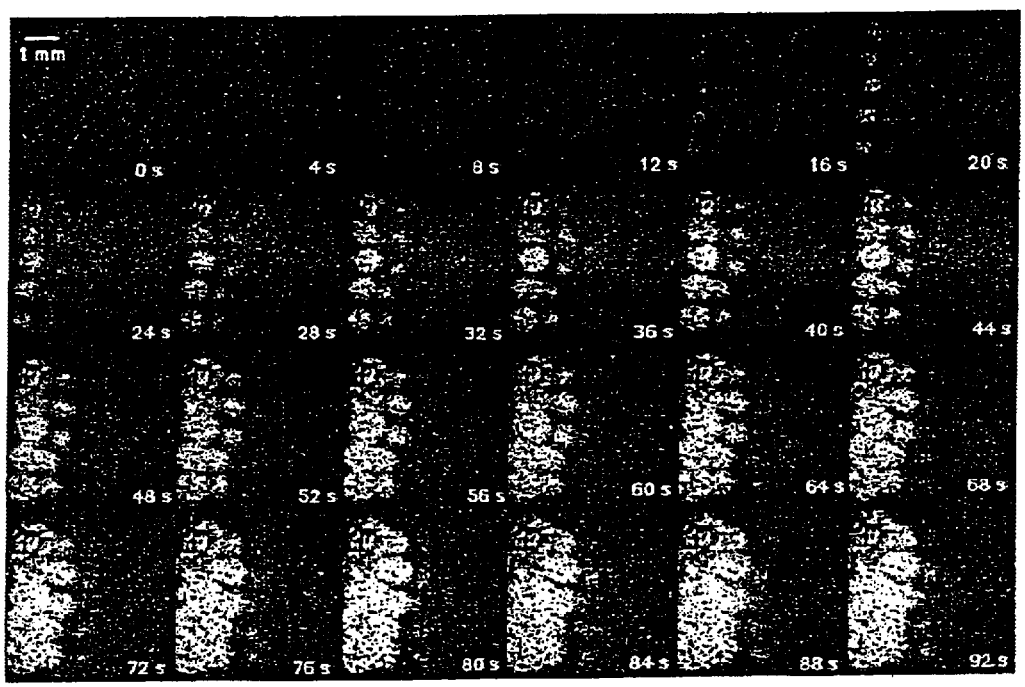
Figure 11:
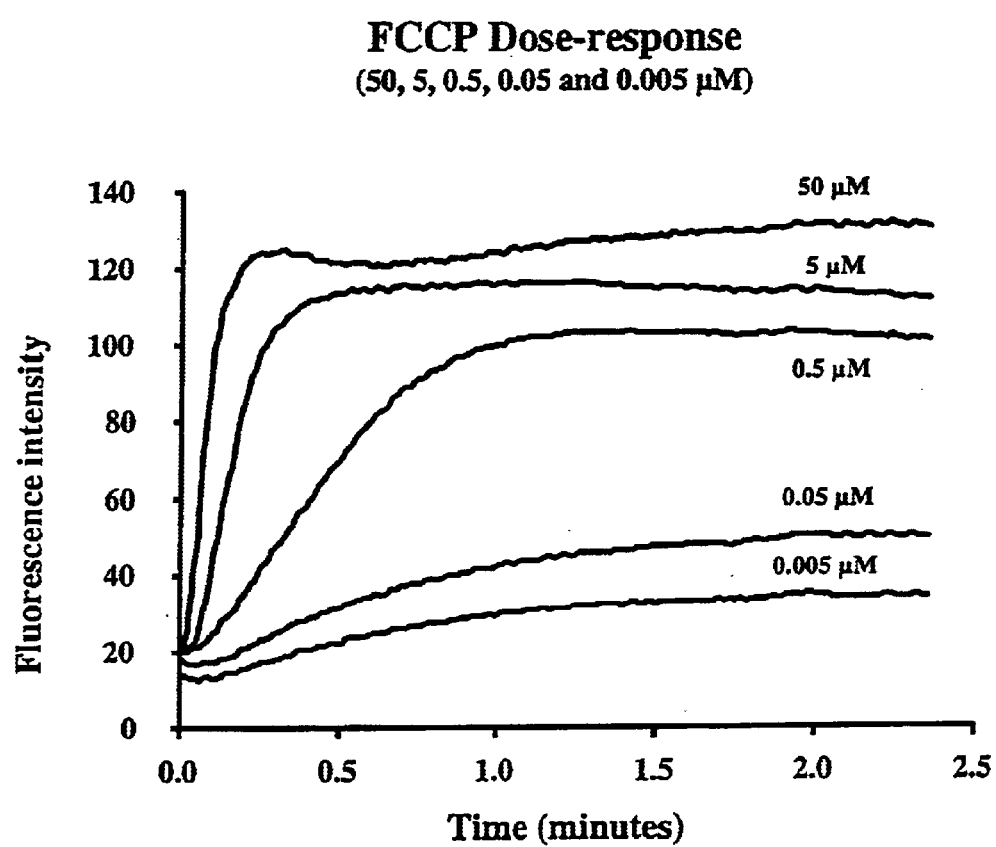

The image series in FIG. 10 shows the response to a membrane grid at five different concentrations of FCCP, the experimental details otherwise being similar to those described for FIGS. 8 and 9. The highest concentration gives the quickest response. Whereas the second and third concentrations also clearly give positive responses with a rise time that is quicker for 5 than 0.5 µM the lower two concentrations do not show detectable responses. The averaged (mean for values from 5 spots per curve) fluorescence intensity time profiles of the five rows of spots in FIG. 10 is displayed in FIG. 11. The three higher concentrations, 50, 5, 0.5 µM give sustained increases and have a rank order for the slope of the initial increase, so that 50>5>0.5>0.05>0.005, although the two lowest concentrations are not significantly different from each other.

Example 9

Response of BHKhM1 Cells Loaded with Fluo-3 to Calcium Ionophore Ionomycin and Thapsigargin.

Figure 12:
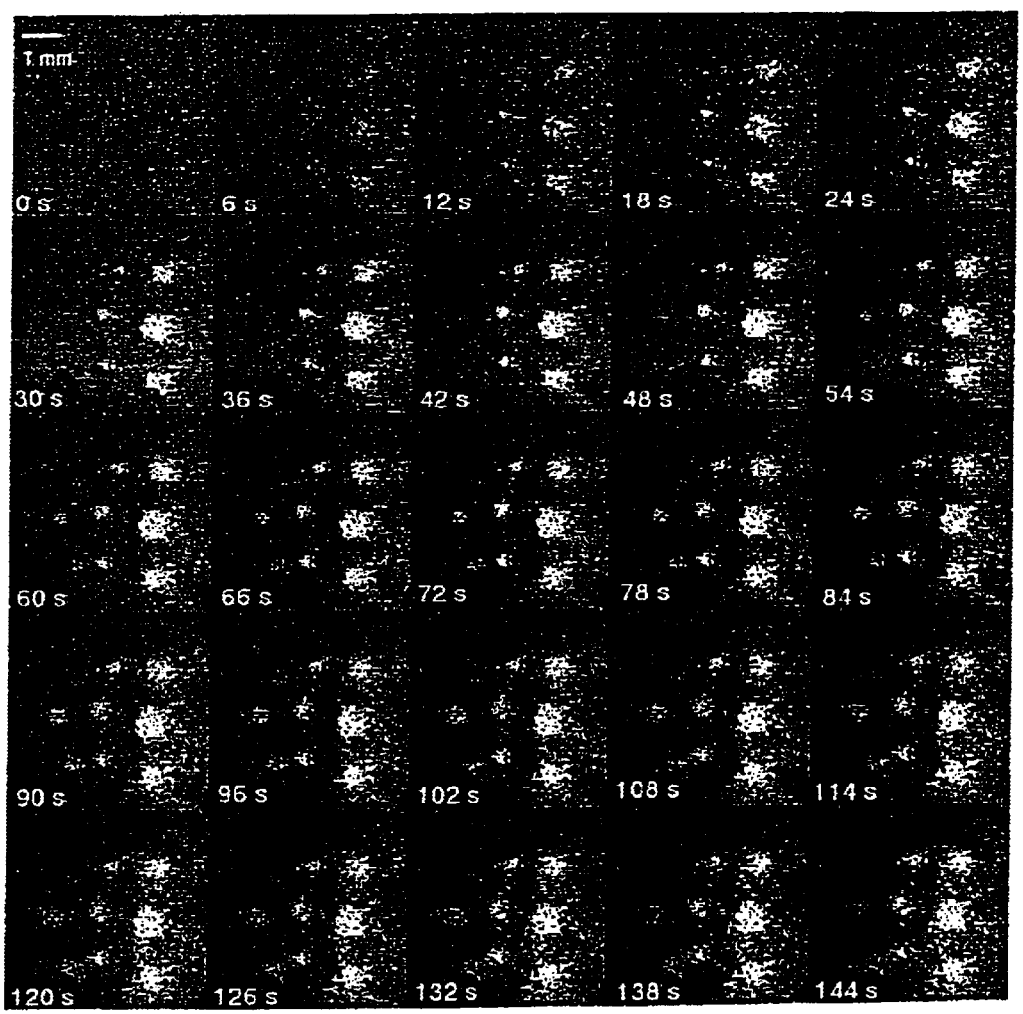
FIGS. 12–13 show the responses of fluo-3 loaded BHKhM1 cells to ionomycin (a calcium ionophore) and thapsigargin (a blocker of the endoplasmic reticulum calcium pump) (Example 9).
Figure 13:
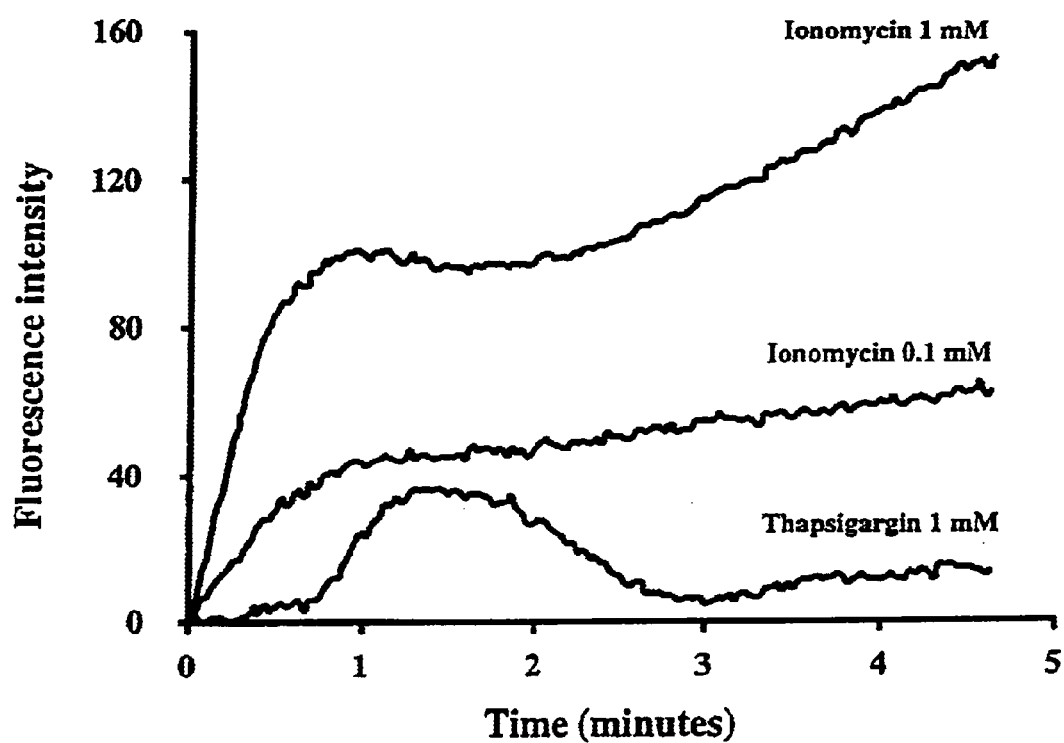

Cells were cultured on porous polyester membranes with 0.3 or 3 µm pore size (Transwells, Corning Costar Corp., Cambridge, Mass., USA) to near confluence (>90%) in DMEM 10% FCS, 100 µg/ml streptomycin, 100 IU/ml penicillin and 500 nM Methotrexate to maintain the human Muscarinic receptor type1 construct. The BHKhM1 cells were loaded with 7 µM Fluo-3/AM (Molecular Probes Inc.) for 50–60 min in the presence of 0.02% Pluronic-127 (Molecular Probes Inc.) in KRW at 37° C. After three washes in KRW, the cells were placed on the stage of a Nikon Diaphot epifluorescence microscope and imaged using a 2× plan apochromatic objective and a CCD camera (Princeton Instruments, NY USA). The cells were excited by 450–490 nm light and light emitted from the cells was filtered by a dichroic mirror (505 nm) and an emission filter (510–560 nm). Exposure/integration times of 1.0 s were used and images acquired at 2 s intervals. Ionomycin was printed onto a glass surface at two concentrations (10 mM and 1 mM), and thapsigargin was printed onto the surface at 1 mM. All spots were allowed to dry. The volume of liquid spotted was approx. 10 nanoliters per spot. At the time indicated as 0 s the still-wet membrane with the cells was lowered down onto the glass surface so that the membrane and the glass came in direct contact, thereby dissolving the compounds deposited in the spots. The image series in FIG. 12 shows the response to a compound grid with three spots of ionomycin (10 mM, the three rightmost spots, 1 mM the three central spots) and three spots of thapsigargin (1 mM) on the left. The high dose of Ionomycin gives the earliest, spatially largest, and most intense response, followed by the lower dose of ionomycin. Both of these are sustained responses. The thapsigargin response is transient and lower in intensity than that of either concentration of ionomycin. FIG. 13 shows the time profiles for the averaged response from both of the ionomycin concentrations (n=3) and the averaged thapsigargin response (n=2).

What is claimed is:

1. A method for simultaneously exposing an array of test compounds to a detector layer of physiologically viable cells, comprising:
    (a) providing an array of test compounds, wherein the test compounds are disposed on a support;
    (b) providing a porous membrane, wherein the porous membrane is constructed of a non-absorbent material with pores of regular and defined diameter which traverse the membrane directly from the upper to the lower side;
    (c) bringing the array of test compounds in close apposition with the detector layer so that the porous membrane is in contact with a liquid layer surrounding the detector layer and the porous membrane is in contact with the array of test compounds thereby allowing diffusion of the test compounds through the porous membrane to the detector layer.

2. The method according to claim 1, wherein the support is a non-porous substrate.

3. The method according to claim 1, wherein the physiologically viable cells form a monolayer.

4. The method according to claim 1, wherein the physiologically viable cells are supported by an optically clear substrate.

5. The method according to claim 1, wherein the detector layer is held stationary in the field of view of an optical detector and the array of test compounds is moved into contact with said detector layer during the course of measurement.

6. The method according to claim 1, wherein the array of test compounds is held stationary in the field of view of an optical detector and the detector layer is moved into contact with said array of test compounds during the course of measurement.

7. The method according to claim 1, wherein the array of test compounds is generated on the support by combinatorial chemistry.

8. A method for screening test compounds for bioactivity by simultaneously exposing an array of test compounds to a detector layer of physiologically viable cells, comprising:
    (a) providing an array of test compounds, wherein each compound is disposed on a support;
    (b) providing a porous membrane, wherein the porous membrane is constructed of a non-absorbent material with pores of regular and defined diameter which traverse the membrane directly from the upper to the lower side;
    (c) bringing the array of test compounds in close apposition with the detector layer so that the porous membrane is in contact with a liquid layer surrounding the detector layer and the porous membrane is in contact with the array of test compounds thereby allowing diffusion of the test compounds through the porous membrane to the detector layer; and
    (d) detecting a response of the detector layer to the test compound.

9. The method according to claim 8, wherein the response is recorded by a sequence of images.

10. The method according to claim 8, wherein the detected response is a change in a luminescence property of the physiologically viable cells in the detector layer.

11. The method according to claim 8, wherein the detected response is a change in a fluorescence property of the physiologically viable cells in the detector layer.

12. The method according to claim 8, wherein the support is a non-porous substrate.

13. The method according to claim 8, wherein the physiologically viable cells form a monolayer.

14. The method according to claim 8, wherein the physiologically viable cells are supported by an optically clear substrate.

15. The method according to claim 8, wherein the detector layer is held stationary in the field of view of an optical detector and the array of test compounds is moved into contact with said detector layer during the course of measurement.

16. The method according to claim 8, wherein the array of test compounds is held stationary in the field of view of an optical detector and the detector layer is moved into contact with said array of test compounds during the course of measurement.

17. The method according to claim 8, wherein the array of test compounds is generated on the support by combinatorial chemistry.

* * * * *